United States Patent
Rafka et al.

(10) Patent No.: US 6,329,345 B1
(45) Date of Patent: Dec. 11, 2001

(54) 13-MEMBERED AZALIDES AND THEIR USE AS ANTIBIOTIC AGENTS

(75) Inventors: Robert J. Rafka, Stonington; Barry J. Morton, Gales Ferry; Colman B. Ragan, Mystic; Peter Bertinato, Old Lyme; John P. Dirlam, Gales Ferry; Alan E. Blize, New London; Carl B. Ziegler, East Lyme, all of CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/442,530

(22) Filed: Nov. 18, 1999

Related U.S. Application Data

(60) Provisional application No. 60/109,399, filed on Nov. 20, 1998.

(51) Int. Cl.$^7$ .......................... A61K 31/70; C07M 17/08
(52) U.S. Cl. ............................. 514/28; 514/29; 536/7.2; 536/7.4
(58) Field of Search ............................. 536/7.2, 7.5, 7.3; 514/29, 28

(56) References Cited

U.S. PATENT DOCUMENTS

| | | | |
|---|---|---|---|
| 4,328,334 | 5/1982 | Kobrehel et al. | 536/7.4 |
| 5,106,961 | 4/1992 | Kirst et al. | 536/7.2 |
| 5,250,518 | 10/1993 | Kobrehel et al. | 514/29 |

OTHER PUBLICATIONS

Eric Hunt and John W. Tyler; C–2 Epimerisation in an Erythromycin Derivative. Preparation and NMR Spectroscopic Studies on (2S)–(E)–9–Deoxo–9–methoxyiminoerythromycin A; J. Chem. Soc. Perkin Trans.; (1990); pp. 2157–2162.

Herbert A. Kirst, et al.; Synthesis of Ring–Contracted Derivatives of Erythromycin; J. Org. Chem.; (1987); pp. 4359–4362.

Issac O. Kibwage, et al.; Translactonization in Erythromycins; J. Org. Chem.; (1987); pp. 990–996.

A. Brian Jones; New Macrolide Antibiotics: Synthesis of a 14–Membered Azalide; J. Org. Chem., vol. 57, No. 16; (1992); pp. 4361–4367.

A. Brain Jones, et al.; The In Vitro Profile of selected 14–Membered Azalides; J. of Antibiotics, vol. 45, No. 11; (1992); pp. 1785–1791.

Sherman T. Waddell, et al.; Chimeric Azalides with Functionalized Western Portions; Heterocycles, vol. 43, No. 11; (1996); pp. 2325–2332.

Robert R. Wilkening, et al.; Novel Transannular Rearrangements of Azalide Iminoethers; TETRAB 53 (50); (1997); pp. 16923–16944.

*Primary Examiner*—Elli Peselev
(74) *Attorney, Agent, or Firm*—Peter C. Richardson; Paul H. Ginsburg; Israel Nissenbaum

(57) ABSTRACT

The invention relates to a method of preparing compounds of the formula 1

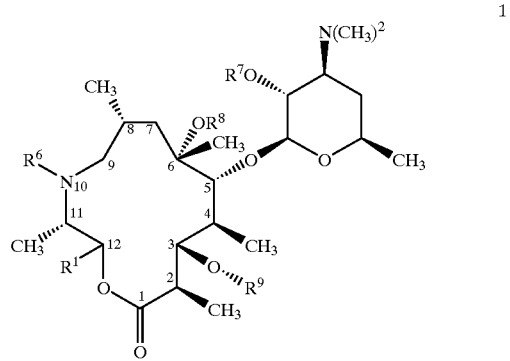

and to pharmaceutically acceptable salts thereof. The compounds of formula 1 are antibacterial agents that may be used to treat various bacterial and protozoa infections. The invention also relates to pharmaceutical compositions containing the compounds of formula 1 and to methods of treating bacterial protozoa infections by administering the compounds of formula 1. The invention also relates to methods of preparing the compounds of formula 1 and to intermediates useful in such preparation.

34 Claims, No Drawings

13-MEMBERED AZALIDES AND THEIR USE AS ANTIBIOTIC AGENTS

This application claims the benefit of U.S. Provisional Application No. 60/109,399 filed Nov. 20, 1998.

BACKGROUND OF THE INVENTION

This invention relates to novel 13-membered azalides that are useful as antibacterial and antiprotozoa agents in mammals, including man, as well as in fish and birds. This invention also relates to pharmaceutical compositions containing the novel compounds, and to methods of treating bacterial infections and protozoa infections in mammals, fish and birds by administering the novel compounds to mammals, fish and birds requiring such treatment.

Macrolide antibiotics are known to be useful in the treatment of a broad spectrum of bacterial infections and protozoa infections in mammals, fish and birds. Such antibiotics include various derivatives of erythromycin A, such as azithromycin. Azithromycin is commercially available, and is referred to in U.S. Pat. Nos. 4,474,768 and 4,517,359, both of which are incorporated herein by reference in their entirety.

Additional macrolides are referred to in U.S. patent application serial No. 60/063676, filed Oct. 29, 1997 (Yong-Jin Wu), U.S. application serial No. 60/063161, filed Oct. 29, 1997 (Yong- Jin Wu), U.S. application serial No. 60/054866, filed Aug. 6, 1997 (Hiroko Masamune, Yong-Jin Wu, Takushi Kaneko and Paul R. McGuirk), U.S. application serial No. 60/049980, filed Jun. 11, 1997 (Brian S. Bronk, Michael A. Letavic, Takushi Kaneko and Bingwei V. Yang), International Application No. PCT/IB98/00839, filed May 29, 1998 (Brian S. Bronk, Hengmiao Cheng, E. A. Glazer, Michael A. Letavic, Takushi Kaneko and Bingwei V. Yang), U.S. application serial No. 60/049348, filed Jun. 11, 1997 (Brian S. Bronk, Hengmiao Cheng, E. A. Glazer, Michael A. Letavic, Takushi Kaneko and Bingwei V. Yang), International Application No. PCT/GB97/01810 filed Jul. 4, 1997 (Peter Francis Leadlay, James Stauton, Jesus Cortes and Michael Stephen Pacey), International Application No. PCT/GB97/01819 filed Jul. 4, 1997 (Peter Francis Leadlay, James Staunton, and Jesus Cortes), U.S. application serial No., 60/070358, filed Jan. 2, 1998 (Yong-Jin Wu), U.S. application serial No. 60/070343, filed Jan. 2, 1998 (Dirlam) and U.S. application serial No. 60/097075, filed Aug. 19, 1998 (Hengmiao Cheng, Michael A. Letavic, Carl B. Ziegler, Jason K. Dutra, Brian S. Bronk), all of which are incorporated herein by reference in their entirety.

Without admitting that the above cited patents and patent applications are prior art to the present application, there remains a need in the art for readily available, 13-membered azalide antibiotic compounds that possess potent activity against a broad range of bacteria and protozoa.

Like azithromycin and other macrolide antibiotics, the novel macrolide compounds of the present invention possess potent activity against various bacterial and protozoa infections as described below.

SUMMARY OF THE INVENTION

The present invention relates to a compound of the formula 1

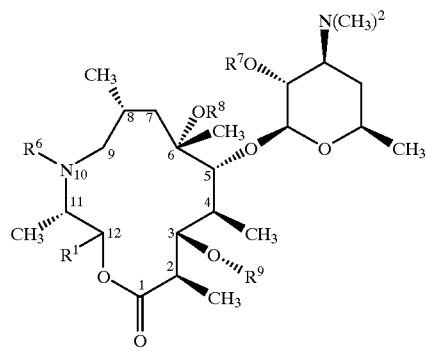

or a pharmaceutically acceptable salt thereof, wherein:

$R^1$ is 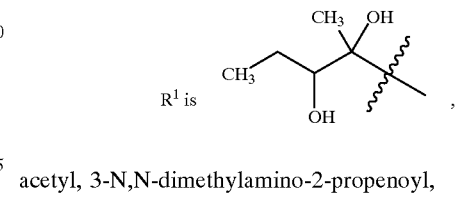

acetyl, 3-N,N-dimethylamino-2-propenoyl,

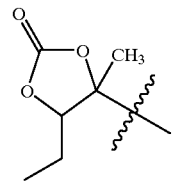

1-N-methyl-5-pyrazolyl, 3-pyrazolyl, 1-methyl-N3-pyrazolyl, 1-N-benzyl-3-pyrazolyl, 1-N-(3-hydroxybenzyl)-3-pyrazolyl, 3-isoxazolyl,

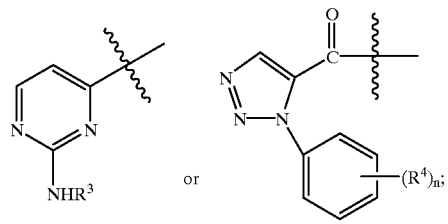

$R^2$ is hydrogen or $C_1$–$C_4$ alkyl;

$R^3$ is hydrogen, $C_1$–$C_{10}$ alkyl, $C_2$–$C_{10}$ alkenyl, $C_2$–$C_{10}$ alkynyl, —$(CH_2)_m(C_6$–$C_{10}$ aryl), -$(CH_2)_m(C_6$–$C_{10}$ heterocyclic) or aryl, each, other than hydrogen, being optionally substituted with 1 to 3 substituents independently selected from halogen, cyano, nitro, trifluoromethyl, azido, —C(O)$C_1$–$C_{10}$ alkyl, —C(O)$C_2$–$C_{10}$ alkenyl, —C(O)$C_2$–$C_{10}$ alkynyl, —OC(O)$C_1$–$C_{10}$ alkyl, —OC(O)$C_2$–$C_{10}$ alkenyl, —OC(O)$C_2$–$C_{10}$ alkynyl, —N(hydrogen, $C_1$–$C_{10}$ alkyl, $C_2$–$C_{10}$ alkenyl or $C_2$–$C_{10}$ alkynyl)C(O)($C_1$–$C_{10}$ alkyl, $C_2$–$C_{10}$ alkenyl or $C_2$–$C_{10}$ alkynyl), —C(O)N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), —N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), $C_1$–$C_{10}$ alkoxy, $C_6$–$C_{10}$ aryl, 5–10 membered heterocyclic, hydroxyl, methoxyl, $C_1$–$C_{10}$ alkyl, $C_2$–$C_{10}$ alkenyl, $C_2$–$C_{10}$ alkynyl, 2-pyridyl, 3-pyridyl, 4-pyridyl, 2-pyrimidyl, 4-pyrimidyl, 2-pyridylmethyl, 3-pyridylmethyl, 4-pyridylmethyl, 2-pyridylethyl, 3-pyridylethyl and 4-pyridylethyl;

m is an integer ranging from 0 to 4;

each $R^4$ is hydrogen, —$(CH_2)_m(C_6$–$C_{10}$ aryl) or —$(CH_2)_m(C_6$–$C_{10}$ heterocyclic), each, other than hydrogen, being optionally substituted with 1 to 3 substituents independently selected from halo, cyano, nitro, trifluoromethyl, azido, —C(O)$C_1$–$C_{10}$ alkyl, —C(O)$C_2$–$C_{10}$ alkenyl, —C(O)$C_2$–$C_{10}$ alkynyl, —OC(O)$C_1$–$C_{10}$ alkyl, —OC(O)$C_2$–$C_{10}$ alkenyl, —OC(O)$C_2$–$C_{10}$ alkynyl, —N(hydrogen, $C_1$–$C_{10}$ alkyl, $C_2$–$C_{10}$ alkenyl or $C_2$–$C_{10}$ alkynyl)C(O)($C_1$–$C_{10}$ alkyl, $C_2$–$C_{10}$ alkenyl or $C_2$–$C_{10}$ alkynyl), —C(O)N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), —N(hydrogen, $C_1$–$C_{10}$ alkyl, $C_2$–$C_{10}$ alkenyl, or $C_2$–$C_{10}$ alkynyl)(hydrogen, $C_{1-10}$ alkyl, $C_1$–$C_{10}$ alkenyl or $C_2$–$C_{10}$ alkynyl), $C_1$–$C_{10}$ alkoxy, $C_6$–$C_{10}$ aryl and 5–10 membered heterocyclic;

n is an integer from 0 to 5;

$R^6$ is hydrogen or methyl;

each $R^7$ is independently hydrogen, $C_1$–$C_{20}$ alkyl, $C_2$–$C_{20}$ alkenyl, $C_2$–$C_{20}$ alkynyl, —(O)$C_1$–$C_{20}$ alkyl, —C(O)$C_2$–$C_{20}$ alkenyl, —C(O)$C_2$–$C_{20}$ alkynyl, —C(O)N(H)$C_1$–$C_{10}$ alkyl, —C(O)N(H)$C_2C_{20}$ alkenyl, —C(O)N(H)$C_2$–$C_{20}$ alkynyl, —$SO_2(O)C_1$–$C_{20}$ alkyl, —$SO_2(O)C_2$–$C_{20}$ alkenyl, —$SO_2(O)C_2$–$C_{20}$alkynyl or —$PO_4^{2-}$;

$R^8$ is hydrogen or methyl;

$R^9$ is

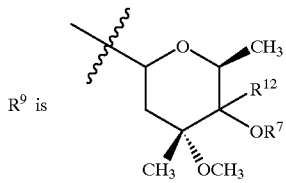

or 4″-oxocladinosyl; and $R^{12}$ is $C_1$–$C_{10}$ alkyl, $C_2$–$C_{10}$ alkenyl, $C_2$–$C_{10}$ alkynyl, cyano, —$CH_2S(O)_pC_{10}$–$C_{10}$ alkyl, —$CH_2S(O)_pC_2$–$C_{10}$ alkenyl, —$CH_2S(O)_pC_2$–$C_{10}$ alkynyl, wherein p is an integer ranging from 0 to 2, —$CH_2O(C_1$–$C_{10}$ alkyl), —$CH_2O(C_2$–$C_{10}$ alkenyl), —$CH_2O(C_2$–$C_{10}$ alkynyl), —$CH_2N$(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), —$(CH_2)_m(C_6$–$C_{10}$ aryl) or —$(CH_2)_m$(5–10 membered heteroaryl), wherein m is an integer ranging from 0 to 4, and wherein the alkyl, alkenyl, alkynyl, aryl and heteroaryl moieties of the foregoing are optionally substituted with 1 to 3 substituents independently selected from halo, cyano, nitro, trifluoromethyl, azido, —C(O)$C_1$–$C_{10}$ alkyl, —C(O)$C_2$–$C_{10}$ alkenyl, —C(O)$C_2$–$C_{10}$ alkynyl, —OC(O)$C_1$–$C_{10}$ alkyl, —OC(O)$C_2$–$C_{10}$ alkenyl, —OC(O)$C_2$–$C_{10}$ alkynyl, —N(hydrogen, $C_1$–$C_{10}$ alkyl, $C_2$–$C_{10}$ alkenyl or $C_2$–$C_{10}$ alkynyl)C(O)($C_1$–$C_{10}$ alkyl, $C_2$–$C_{10}$ alkenyl or $C_2$–$C_{10}$ alkynyl), —C(O)N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), —N($C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), $C_1$–$C_{10}$ alkoxy, $C_6$–$C_{10}$ aryl or 5–10 membered heterocyclic, hydroxy, $C_1$–$C_6$ alkyl, $C_2$–$C_6$ alkoxy, $C_6$–$C_{10}$ aryl and 5–10 membered heteroaryl.

The present invention further relates to a compound of the formula 15

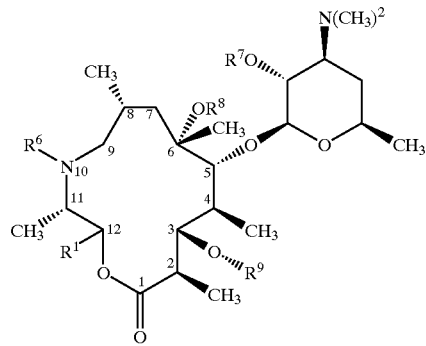

or a pharmaceutically acceptable salt thereof, wherein:

$R^1$ is 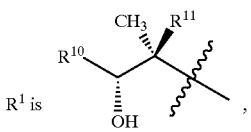, acetyl, 3-N,N-dimethylamino-2-propenoyl,

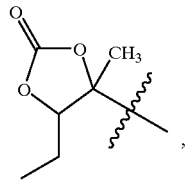,

1-N-methyl-5-pyrazolyl, 3-pyrazolyl, 1-methyl-N-3-pyrazolyl, 1-N-benzyl-3-pyrazolyl, 1-N-(3-hydroxybenzyl)-3-pyrazolyl, 3-isoxazolyl,

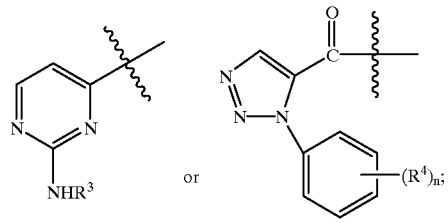

$R^2$ is hydrogen or $C_1$–$C_4$ alkyl;

$R^3$ is hydrogen, $C_1$–$C_{10}$ alkyl, $C_2$–$C_{10}$ alkenyl, $C_2$–$C_{10}$ alkynyl, —$(CH_2)_m(C_6$–$C_{10}$ aryl), —$(CH_2)_m(C_6$–$C_{10}$ heterocyclic) or aryl, each, other than hydrogen, being optionally substituted with 1 to 3 substituents independently selected from halogen, cyano, nitro, trifluoromethyl, azido, —C(O)$C_1$–$C_{10}$ alkyl, —C(O)$C_2$–$C_{10}$ alkenyl, —C(O)$C_2$–$C_{10}$ alkynyl, —OC(O)$C_1$–$C_{10}$ alkyl, —OC(O)$C_2$–$C_{10}$alkenyl, —OC(O)$C_2$–$C_{10}$ alkynyl, —N(hydrogen, $C_1$–$C_{10}$ alkyl, $C_2$–$C_{10}$alkenyl or $C_2$–$C_{10}$ alkynyl)C(O)($C_{10}$–$C_{10}$ alkyl, $C_2$–$C_{10}$ alkenyl or $C_2$–$C_{10}$ alkynyl), —C(O)N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), —N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), $C_1$–$C_{10}$ alkoxy, $C_6$–$C_{10}$ aryl, 5–10 membered heterocyclic, hydroxyl, methoxyl, $C_1$–$C_{10}$ alkyl, $C_2$–$C_{10}$ alkenyl, $C_2$–$C_{10}$ alkynyl, 2-pyridyl, 3-pyridyl, 4-pyridyl, 2-pyrimidyl, 4-pyrimidyl, 2-pyridylmethyl, 3-pyridylmethyl, 4-pyridylmethyl, 2-pyridylethyl, 3-pyridylethyl and 4-pyridylethyl;

m is an integer ranging from 0 to 4;

each $R^4$ is hydrogen, —$(CH_2)_m(C_6$–$C_{10}$ aryl) or —$(CH_2)_m(C_6$–$C_{10}$ heterocyclic), each, other than hydrogen, being optionally substituted with 1 to 3 substituents independently selected from halo, cyano, nitro, trifluoromethyl, azido, —C(O)$C_1$–$C_{10}$ alkyl, —C(O)$C_2$–$C_{10}$ alkenyl, —C(O)$C_2$–$C_{10}$ alkynyl, —OC(O)$C_1$–$C_{10}$ alkyl, —OC(O)$C_2$–$C_{10}$ alkenyl, —OC(O)$C_2$–$C_{10}$ alkynyl, —N(hydrogen, $C_1$–$C_{10}$ alkyl, $C_2$–$C_{10}$ alkenyl or $C_2$–$C_{10}$ alkynyl)C(O)($C_1$–$C_{10}$ alkyl, $C_2$–$C_{10}$ alkenyl or $C_2$–$C_{10}$ alkynyl), —C(O)N(hydrogen, $C_1$–$C_{10}$alkyl, $C_2$–$C_{10}$ alkenyl or $C_2$–$C_{10}$ alkynyl) (hydrogen, $C_1$–$C_{10}$ alkyl, $C_2$–$C_{10}$ alkenyl or $C_2$–$C_{10}$ alkynyl), —N(hydrogen, $C_1$–$C_{10}$ alkyl, $C_2$–$C_{10}$ alkenyl or $C_2$–$C_{10}$ alkynyl)(hydrogen, $C_1C_{10}$ alkyl, $C_2$–$C_{10}$ alkenyl or $C_2$–$C_{10}$ alkynyl), $C_1$–$C_{10}$ alkoxy, aryl and 5–10 membered heterocyclic;

n is an integer from 0 to 5;

$R^6$ is hydrogen or methyl;

each $R^7$ is independently hydrogen, $C_1$–$C_{20}$ alkyl, $C_2$–$C_{20}$ alkenyl, $C_2$–$C_{20}$ alkynyl, —C(O)$C_1$–$C_{20}$ alkyl, —C(O)$C_2$–$C_{20}$ alkenyl, —C(O)$C_2$–$C_{20}$ alkynyl, —C(O)N(H)$C_1$–$C_{10}$ alkyl, —C(O)N(H)$C_2$–$C_{20}$ alkenyl, —C(O)N(H)$C_2$–$C_{20}$ alkynyl, —$SO_2$(O)$C_1$–$C_{20}$ alkyl, —$SO_2$(O)$C_{2-C20}$ alkenyl, —$SO_2$(O)$C_2$–$C_{20}$ alkynyl or —$PO_4^{2-}$;

$R^8$ is hydrogen or methyl;

$R^9$ is

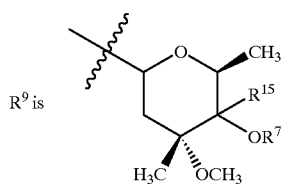

or 4"-oxocladinosyl;

$R^{10}$ is an alpha-branched $C_2$–$C_8$ alkyl, alkenyl, alkynyl, alkoxyalkyl or alkylthioalkyl group, any of which may optionally be substituted by one or more hydroxyl groups; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methyl or one or more hydroxyl, one or more $C_1$–$C_4$ alkyl groups or halo atoms; or a 3 to 6 membered oxygen or sulphur containing heterocyclic ring which may be saturated, or fully or partially unsaturated and which may optionally be substituted by one or more $C_1$–$C_4$ alkyl groups or halo atoms; or $R^{10}$ is phenyl which may be optionally substituted with at least one substituent selected from $C_1$–$C_4$ alkyl, $C_1$–$C_4$ alkylthio groups, halogen atoms, hydroxyl groups, trifluoromethyl, and cyano; or $R^{10}$ may be with a formula (a) as shown below:

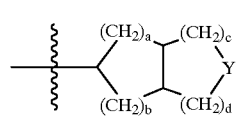

a wherein Y is O, S or —$CH_2$—, a, b, c, and d is each independently an integer ranging from 0–2 and a+b+c+d≦5;

$R^{11}$ is hydrogen or —OH; and $R^{15}$ is H, $C_1$–$C_{10}$ alkyl, $C_2$–$C_{10}$ alkenyl, $C_2$–$C_{10}$ alkynyl, cyano, —$CH_2S(O)_p C_1$–$C_{10}$ alkyl, —$CH_2S(O)_p C_2$–$C_{10}$ alkenyl, —$CH_2S(O)_p C_2$–$C_{10}$ alkynyl, wherein p is an integer ranging from 0 to 2, —$CH_2O$($C_1$–$C_{10}$ alkyl), —$CH_2O$($C_2$–$C_{10}$ alkenyl), —$CH_2O$($C_2$–$C_{10}$ alkynyl), —$CH_2$N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), —$(CH_2)_m(C_6$–$C_{10}$ aryl) or —$(CH_2)_m$(5–10 membered heteroaryl), wherein m is an integer ranging from 0 to 4, and wherein the alkyl, alkenyl, alkynyl, aryl and heteroaryl moieties of the foregoing are optionally substituted with 1 to 3 substituents independently selected from halo, cyano, nitro, trifluoromethyl, azido, —C(O)$C_1$–$C_{10}$ alkyl, —C(O)$C_2$–$C_{10}$ alkenyl, —C(O)$C_2$–$C_{10}$ alkynyl, —OC(O)$C_1$–$C_{10}$ alkyl, —OC(O)$C_2$–$C_{10}$ alkenyl, —OC(O)$C_2$–$C_{10}$ alkynyl, —N(hydrogen, $C_1$–$C_{10}$ alkyl, $C_2$–$C_{10}$ alkenyl or $C_2$–$C_{10}$ alkynyl)C(O)($C_1$–$C_{10}$ alkyl, $C_2$–$C_{10}$ alkenyl or $C_2$–$C_{10}$ alkynyl), —C(O)N(hydrogen, $C_1$–$C_{10}$ alkyl, $C_2$–$C_{10}$ alkenyl or $C_2$–$C_{10}$ alkynyl) (hydrogen, $C_1$–$C_{10}$ alkyl, $C_2$–$C_{10}$ alkenyl or $C_2$–$C_{10}$ alkynyl), —N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), $C_1$–$C_{10}$ alkoxy, $C_6$–$C_{10}$ aryl or 5–10 membered heterocyclic, hydroxy, $C_1$–$C_6$ alkyl, $C_1$–$C_8$ alkoxy, $C_6$–$C_{10}$ aryl and 5–10 membered heteroaryl, except that when $R^{15}$ is H, $R^{10}$ is not ethyl.

The present invention also relates to compounds of the formula 2

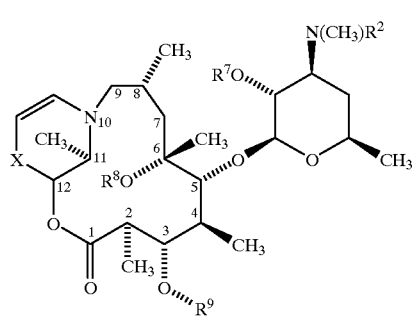

2 and to pharmaceutically acceptable salts thereof, wherein:
X is —C(O)— or —CH(OR$^7$)—; and
R$^2$ and R$^7$ are defined above, and R$^9$ is

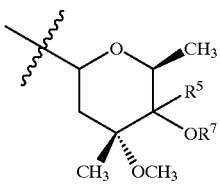

or 4"-oxocladinosyl; and

R$^5$ is hydrogen, $C_1$–$C_{10}$ alkyl, $C_2$–$C_{10}$ alkenyl, $C_2$–$C_{10}$ alkynyl, cyano, —CH$_2$S(O)$_p$C$_1$–C$_{10}$ alkyl, —CH$_2$S(O)$_p$C$_2$–C$_{10}$ alkenyl, —CH$_2$S(O)$_p$C$_2$–C$_{10}$ alkynyl, wherein p is an integer ranging from 0 to 2, —CH$_2$O(C$_1$–C$_{10}$ alkyl), —CH$_2$O(C$_2$–C$_{10}$ alkenyl), —CH$_2$O(C$_2$–C$_{10}$ alkynyl), —CH$_2$N(hydrogen, C$_1$–C$_{10}$ alkyl, C$_2$–C$_{10}$ alkenyl or C$_2$–C$_{10}$ alkynyl)(hydrogen, C$_1$–C$_{10}$ alkyl, C$_2$–C$_{10}$ alkenyl or C$_2$–C$_{10}$ alkynyl), —(CH$_2$)$_m$(C$_6$–C$_{10}$ aryl) or —(CH$_2$)$_m$(5–10 membered heteroaryl), wherein m is an integer ranging from 0 to 4, and wherein the alkyl, alkenyl, alkynyl, aryl and heteroaryl moieties of the foregoing are optionally substituted with 1 to 3 substituents independently selected from halo, cyano, nitro, trifluoromethyl, azido, —C(O)C$_1$–C$_{10}$ alkyl, —C(O)C$_2$–C$_{10}$ alkenyl, —C(O) C$_2$–C$_{10}$ alkynyl, —OC(O)C$_2$–C$_{10}$ alkyl, —OC(O) C$_2$–C$_{10}$ alkenyl, —OC(O)C$_2$–C$_{10}$ alkynyl, —N(hydrogen, C$_1$–C$_{10}$ alkyl, C$_2$–C$_{10}$ alkenyl or C$_2$–C$_{10}$ alkynyl)C(O)(C$_1$–C$_{10}$ alkyl, C$_2$–C$_{10}$ alkenyl or C$_2$–C$_{10}$ alkynyl), —C(O)N(hydrogen, C$_1$–C$_{10}$ alkyl, C$_2$–C$_{10}$ alkenyl or C$_2$–C$_{10}$ alkynyl)(hydrogen, C$_1$–C$_{10}$ alkyl, C$_2$–C$_{10}$ alkenyl or C$_2$–C$_{10}$ alkynyl), —N(hydrogen, C$_1$–C$_{10}$ alkyl, C$_2$–C$_{10}$ alkenyl or C$_2$–C$_{10}$ alkynyl)(hydrogen, C$_1$–C$_{10}$ alkyl, C$_2$–C$_{10}$ alkenyl or C$_2$–C$_{10}$ alkynyl), C$_1$–C$_{10}$ alkoxy, C$_6$–C$_{10}$ aryl or 5–10 membered heterocyclic, hydroxy, C$_1$C$_6$ alkyl, C$_1$C$_6$ alkoxy, C$_6$–C$_{10}$ aryl and 5–10 membered heteroaryl.

Preferred compounds of formula 2 include those wherein R$^7$ and R$^8$ are hydrogen, and R$^9$ is

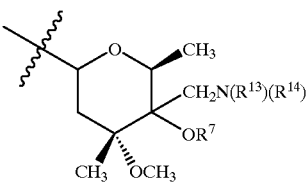

The compounds of formula 1 and formula 2 are preferably in their isolated or purified form.

The invention also relates to a pharmaceutical composition which can be used for the treatment of a bacterial infection or a protozoa infection in a mammal, fish, or bird which comprises a therapeutically effective amount of a compound of formula 1, formula 2, or formula 15 or a pharmaceutically acceptable salt thereof, and a pharmaceutically acceptable carrier.

The invention also relates to a method of treating a bacterial infection or a protozoa infection in a mammal, fish, or bird which comprises administering to said mammal, fish or bird a therapeutically effective amount of a compound of formula 1, formula 2 or formula 15 or a pharmaceutically acceptable salt thereof.

In a preferred embodiment, the compound of formula 1 is that wherein R$^1$=

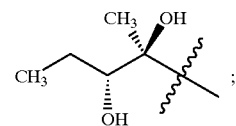

R$^6$, R$^7$ and R$^8$=hydrogen; and R$^9$=4"-((R$^{13}$)(R$^{14}$)NCH$_2$) cladinosyl.

The term "treatment", as used herein, unless otherwise indicated, includes the treatment or prevention of a bacterial infection or protozoa infection as provided in the method of the present invention.

As used herein, unless otherwise indicated, the terms "bacterial infection(s)" and "protozoa infection(s)" include bacterial infections and protozoa infections that occur in mammals, fish and birds as well as disorders related to bacterial infections and protozoa infections that may be treated or prevented by administering antibiotics such as the compounds of the present invention. Such bacterial infections and protozoa infections, and disorders related to such infections, include the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus,* or *Peptostreptococcus* spp.; pharynigitis, rheumatic fever, and glomerulonephritis related to infection by *Streptococcus pyogenes,* Groups C and *G streptococci, Clostridium diptheriae,* or *Actinobacillus haemolyticum;* respiratory tract infections related to infection by *Mycoplasma pneumoniae, Legionella pneumophila, Streptococcus pneumoniae, Haemophilus influenzae,* or *Chlamydia pneumoniae;* uncomplicated skin and soft tissue infections, abscesses and osteomyelitis, and puerperal fever related to infection by *Staphylococcus aureus,* coagulase-positive staphylococci (i.e., *S. epidermidis, S. hemolyticus,* etc.), *Streptococcus pyogenes, Streptococcus agalactiae,* Streptococcal groups C-F (minute-colony streptococci), viridans streptococci, *Corynebacterium minutissimum,* Clostridium spp., or *Bartonella henselae;* uncomplicated acute urinary tract infections related to infection by *Staphylococcus saprophyticus* or *Enterococcus* spp.; urethritis and cervicitis; and sexually transmitted diseases related to infection by *Chlamydia trachomatis, Haemophilus ducreyi, Treponema pallidum, Ureaplasma urealyticum,* or *Neiserria gonorrheae;* toxin diseases related to infection by *S. aureus* (food poisoning and Toxic shock syndrome), or Groups A, B, and C streptococci; ulcers related to infection by *Helicobacter pylori;* systemic febrile syndromes related to infection by *Borrelia recurrentis;* Lyme disease related to infection by *Borrelia burgdorferi;* conjunctivitis, keratitis, and dacrocystitis related to infection by *Chlamydia trachomatis, Neisseria gonorrhoeae, S. aureus, S. pneumoniae, S. pyogenes, H. influenzae,* or *Listeria* spp.; disseminated Mycobacterium avium complex (MAC) disease related to infection by *Mycobacterium avium,* or *Mycobacterium intracellulare;* gastroenteritis related to infection by *Campylobacter jejuni;* intestinal protozoa related to infection by Cryptosporidium spp.; odontogenic infection related to infection by viridans streptococci; persistent cough related to infection by *Bordetella pertussis;* gas gangrene related to infection by *Clostridium perfringensor* Bacteroides spp.; and atherosclerosis related to infection by *Helicobacter pylori* or *Chlamydia pneumoniae.* Bacterial infections and protozoa infections and disorders related to such infections that may be treated or prevented in animals include the following: bovine respiratory disease related to infection by *P. haem.,*

P. multocida, Mycoplasma bovis, or Bordetella spp.; cow enteric disease related to infection by E. coli or protozoa (i.e., coccidia, cryptosporidia, etc.); dairy cow mastitis related to infection by Staph. aureus, Strep. uberis, Strep. agalactiae, Strep. dysgalactiae, Klebsiella spp., Corynebacterium, or Enterococcus spp.; swine respiratory disease related to infection by A. pleuro., P. multocida, or Mycoplasma spp.; swine enteric disease related to infection by E coli, Lawsonia intracellularis, Salmonella, or Serpulina hyodyisinteriae; cow footrot related to infection by Fusobacterium spp.; cow metritis related to infection by E coli; cow hairy warts related to infection by Fusobacterium necrophorum or Bacteroides nodosus; cow pink-eye related to infection by Moraxella bovis; cow premature abortion related to infection by protozoa (i.e. neosporium); urinary tract infection in dogs and cats related to infection by E coli; skin and soft tissue infections in dogs and cats related to infection by Staph. epidermidis, Staph. intermedius, coagulase neg. Staph. or P. multocida; and dental or mouth infections in dogs and cats related to infection by Alcaligenes spp., Bacteroides spp., Clostridium spp., Enterobacter spp., Eubacterium, Peptostreptococcus, Porphyromonas, or Prevotella. Other bacterial infections and protozoa infections and disorders related to such infections that may be treated or prevented in accord with the method of the present invention are referred to in J. P. Sanford et al., "The Sanford Guide To Antimicrobial Therapy," 26th Edition, (Antimicrobial Therapy, Inc., 1996).

The present invention also relates to a method of preparing a compound of formula 1 particularly wherein $R^6$, $R^7$ and $R^8$ are hydrogen, and $R^1$ is trans with respect to the methyl group at position 11 of formula 1, or a pharmaceutically acceptable salt thereof, which comprises the step of contacting compound of the formula 5

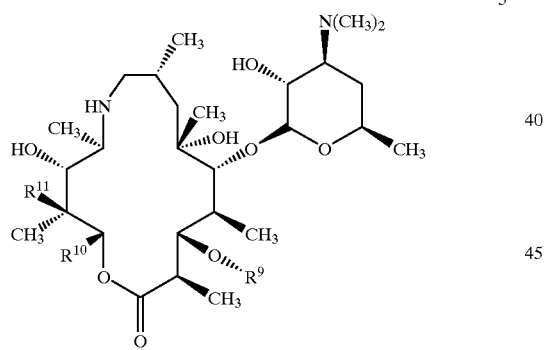

wherein $R^9$, is as defined for formula 1;

$R^{10}$ is an alpha-branched $C_2$–$C_8$ alkyl, alkenyl, alkynyl, alkoxyalkyl or alkylthioalkyl group, any of which may optionally be substituted by one or more hydroxyl groups; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methyl or one or more hydroxyl, one or more $C_1$–$C_4$ alkyl groups or halo atoms; or a 3 to 6 membered oxygen or sulphur containing heterocyclic ring which may be saturated, or fully or partially unsaturated and which may optionally be substituted by one or more $C_1$–$C_4$ alkyl groups or halo atoms; or $R^{10}$ is phenyl which may be optionally substituted with at least one substituent selected from $C_1$–$C_4$ alkyl, $C_1$–$C_4$ alkylthio groups, halogen atoms, hydroxyl groups, trifluoromethyl, and cyano; or $R^{10}$ may be with a formula (a) as shown below:

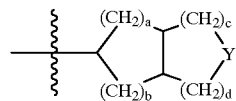

wherein

Y is O, S or —$CH_2$—, a, b, c, and d is each independently an integer ranging from 0–2 and a+b+c+d≦5; and $R^{11}$ is hydrogen or —OH, with an acid or a base to result in the formation of a compound of formula 1.

The present invention further relates to a method of preparing a compound of formula 1, particularly wherein $R^6$, $R^7$ and $R^8$ are hydrogen, and $R^1$ is trans with respect to the methyl group at position 11 of formula 1, or a pharmaceutically acceptable salt thereof, which comprises the step of heating a compound of the formula 5 in the presence of a solvent to result in the formation of a compound of formula 1.

The present invention also relates to a method of preparing a compound of formula 15 particularly wherein $R^6$, $R^7$ and $R^8$ a are hydrogen, and $R^1$ is trans with respect to the methyl group at position 11 of formula 15, or a pharmaceutically acceptable salt thereof, which comprises the step of contacting compound of the formula 5

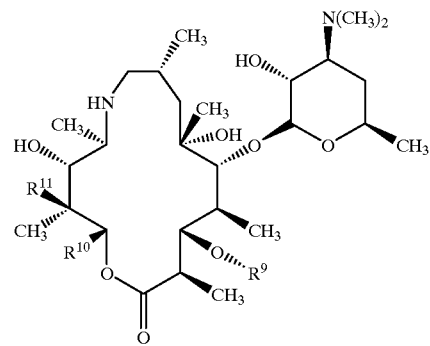

wherein $R^9$ is as defined for formula 15;

$R^{10}$ is an alpha-branched $C_2$–$C_8$ alkyl, alkenyl, alkynyl, alkoxyalkyl or alkylthioalkyl group, any of which may optionally be substituted by one or more hydroxyl groups; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methyl or one or more hydroxyl, one or more $C_1$–$C_4$ alkyl groups or halo atoms; or a 3 to 6 membered oxygen or sulphur containing heterocyclic ring which may be saturated, or fully or partially unsaturated and which may optionally be substituted by one or more $C_1$–$C_4$ alkyl groups or halo atoms; or $R^{10}$ is phenyl which may be optionally substituted with at least one substituent selected from $C_1$–$C_4$ alkyl, $C_1$–$C_4$ alkylthio groups, halogen atoms, hydroxyl groups, trifluoromethyl, and cyano; or $R^{10}$ may be with a formula (a) as shown below:

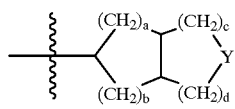

wherein
Y is O, S or —$CH_2$—, a, b, c, and d is each independently an integer ranging from 0–2 and a+b+c+d≦5; and
$R^{11}$ is hydrogen or —OH,
with an acid or a base to result in the formation of a compound of formula 15.

The present invention further relates to a method of preparing a compound of formula 15, particularly wherein $R^6$, $R^7$ and $R^8$ are hydrogen, and $R^1$ is trans with respect to the methyl group at position 11 of formula 15, or a pharmaceutically acceptable salt thereof, which comprises the step of heating a compound of the formula 5 in the presence of a solvent to result in the formation of a compound of formula 15.

Preferred compounds of formula 5 are those in which $R^{10}$ is ethyl, isopropyl, cyclopropyl, sec-butyl, cyclobutyl, cyclopentyl, methylthioethyl or furyl, and $R^{11}$ is hydrogen; and those in which $R^{10}$ is cyclopropyl or cyclobutyl, and $R^{11}$ is —OH.

The present invention also relates to the above compounds of formula 5 which, as indicated above, are useful in the preparation of the above compounds of formula 1 or 15 and pharmaceutically acceptable salts thereof.

The term "hydroxy protecting group", as used herein, unless otherwise indicated, includes acetyl, benzyloxycarbonyl, and various hydroxy protecting groups familiar to those skilled in the art include the groups referred to in T. W. Greene, P. G. M. Wuts, "Protective Groups In Organic Synthesis," (J. Wiley & Sons, 1991).

The term "halo", as used herein, unless otherwise indicated, includes fluoro, chloro, bromo or iodo. Preferred halo groups are fluoro, chloro and bromo.

The term "alkyl", as used herein, unless otherwise indicated, includes saturated monovalent hydrocarbon radicals having straight, cyclic or branched moieties. Such cyclic moieties include cyclopropyl, cyclobutyl and cyclopentyl. The alkyl group may include one or two double or triple bonds. It is to be understood that where cyclic moieties are intended, at least three carbons in said alkyl must be present, and for the alkyl group to include a carbon-carbon double or triple bond, at least two carbon atoms are required in the alkyl group. Where the alkyl moiety is defined as $C_1$–$C_{10}$ alkyl, this group includes $C_6$–$C_{10}$ bicyclo groups such as a bicyclo[3.1.1]heptylmethyl group.

The term "alkoxy", as used herein, unless otherwise indicated, includes —O-alkyl groups wherein alkyl is as defined above.

The term "aryl", as used herein, unless otherwise indicated, includes an organic radical derived from an aromatic hydrocarbon by removal of one hydrogen, such as phenyl or naphthyl, as well as benzo-fused carbocyclic moieties such as 5,6,7,8-tetrahydronaphthyl.

The term "4–10 membered heterocyclic", as used herein, unless otherwise indicated, includes aromatic and non-aromatic heterocyclic groups containing one or more heteroatoms each selected from O, S, and N, wherein each heterocyclic group has from 4–10 atoms in its ring system. Non-aromatic heterocyclic groups include groups having only 4 atoms in their ring system, but aromatic heterocyclic groups must have at least 5 atoms in their ring system. The heterocyclic groups include benzo-fused ring systems, and ring systems substituted with one or two oxo moieties. An example of a 5-membered heterocyclic group is thiazolyl, and an example of a 10-membered heterocyclic group is quinolinyl. Examples of non-aromatic heterocyclic groups are pyrrolidinyl, piperidino, morpholino, thiomorpholino and piperazinyl. Non-aromatic heterocyclic groups include saturated and partially unsaturated ring systems. Examples of aromatic heterocyclic groups are pyridinyl, imidazolyl, pyrimidinyl, pyrazolyl, triazolyl, pyrazinyl, tetrazolyl, furyl, thienyl, isoxazolyl and thiazolyl. Heterocyclic groups having a fused benzene ring include chroman, benzodihydrofuran and benzimidazolyl. Heterocyclic groups having one or two oxo moieties include phthalimide and uracil.

The term "5–10 membered heteroaryl", as used herein, unless otherwise indicated, includes aromatic heterocyclic groups containing one or more heteroatoms each selected from O, S and N, wherein each heterocyclic group has from 5 to 10 atoms in its ring system. Examples of suitable 5–10 membered heteroaryl groups include pyridinyl, imidazolyl, pyrimidinyl, pyrazolyl, (1,2,3,)- and (1,2,4)-triazolyl, pyrazinyl, tetrazolyl, furyl, thienyl, isoxazolyl, oxazolyl, pyrrolyl and thiazolyl.

The term "desosaminyl", as used herein, unless otherwise indicated, refers to the

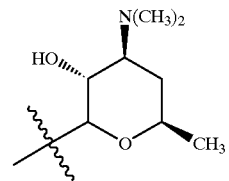

group

The term "cladinosyl", as used herein, unless otherwise indicated, refers to the group

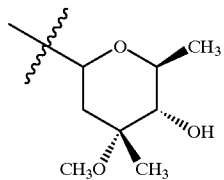

The term "4"—(($R^{13}$)($R^{14}$)$NCH_2$)cladinosyl", as used herein, unless otherwise indicated,

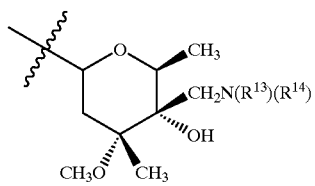

refers to the group

The term "4-oxocladinosyl", as used herein, unless otherwise indicated refers to the

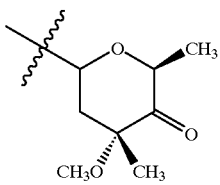

group

The term "isolated or purified form", as used herein, unless otherwise indicated, means isolated or purified from a reaction mixture, e.g., a reaction mixture containing a 15-membered azalide starting material that is then purified to contain at least about 95% of a compound of formula 1; bacterial culture or broth; or natural, e.g., plant or animal, source, e using conventional purification techniques such as chromatography, recrystallization and others known to those skilled in the art, as well as those methods disclosed herein.

The phrase "pharmaceutically acceptable salt(s)", as used herein, unless otherwise indicated, includes salts of acidic or basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of the present invention are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. The compounds of the present invention that include an amino moiety may form pharmaceutically acceptable salts with various amino acids, in addition to the acids mentioned above.

Preferably, the compounds of formula 1 can be used as antibacterial and an antiprotozoa agents when in admixture with the compounds of formula 5. In such a case, the ratio of a compound of formula 1 to a compound of formula 5 ranges from about 2:98 to about 40:60.

Those compounds of the present invention that are acidic in nature are capable of forming base salts with various pharmacologically acceptable cations. Examples of such salts include the alkali metal or alkaline earth metal salts and, particularly, the calcium, magnesium, sodium and potassium salts of the compounds of the present invention.

Certain compounds of the present invention may have asymmetric centers and therefore exist in different enantiomeric and diastereomic forms. This invention relates to the use of all optical isomers and stereoisomers of the compounds of the present invention, and mixtures thereof, and to all pharmaceutical compositions and methods of treatment that may employ or contain them.

The present invention includes the compounds of the present invention, and the pharmaceutically acceptable salts thereof, wherein one or more hydrogen, carbon or other atoms are replaced by isotopes thereof. Such compounds may be useful as research and diagnostic tools in metabolism pharmacokinetic studies and in binding assays.

The present invention may be understood more fully by reference to the detailed description and illustrative examples which are intended to exemplify non-limiting embodiments of the invention.

DETAILED DESCRIPTION OF THE INVENTION

The compounds of the present invention may be prepared according to Schemes 1 and 2 below, and to the description that follows. In the following Schemes, unless otherwise indicated, substituents $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ are as defined above.

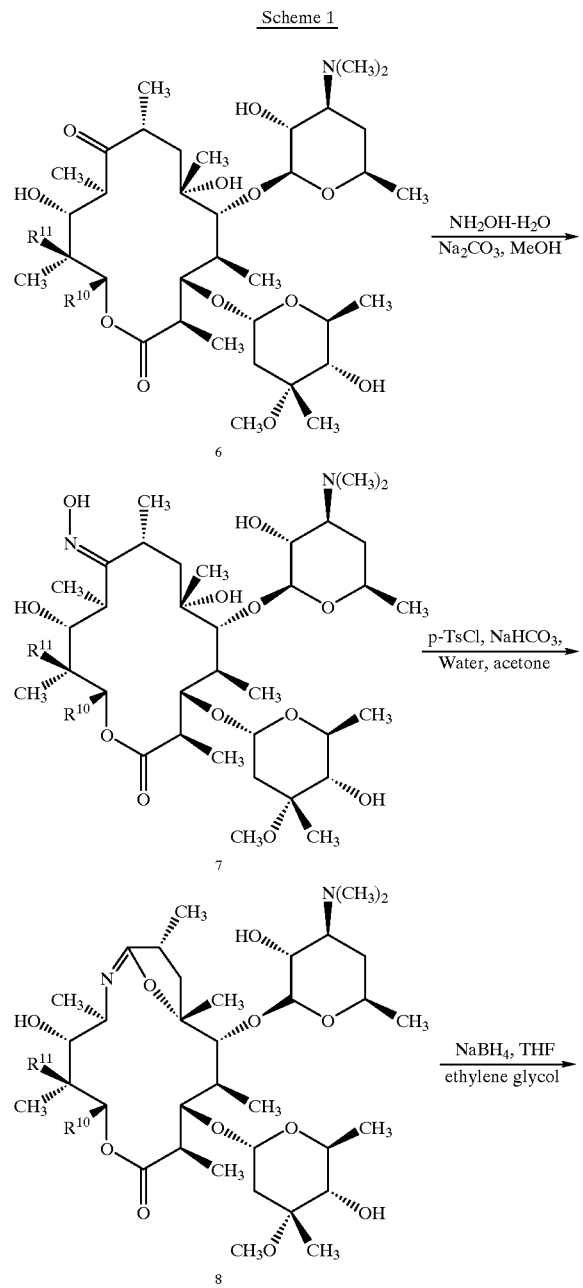

Scheme 2

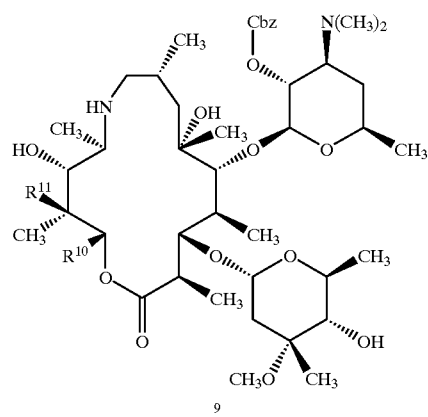

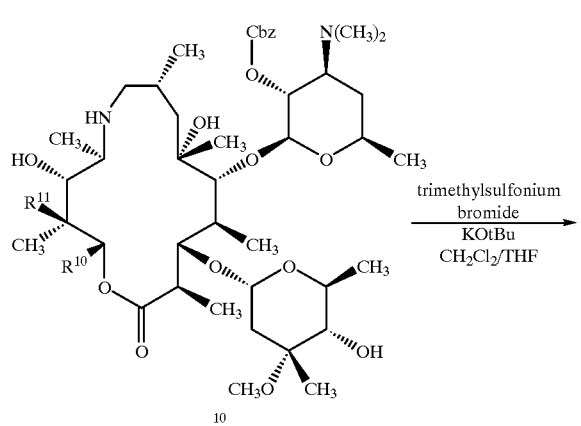

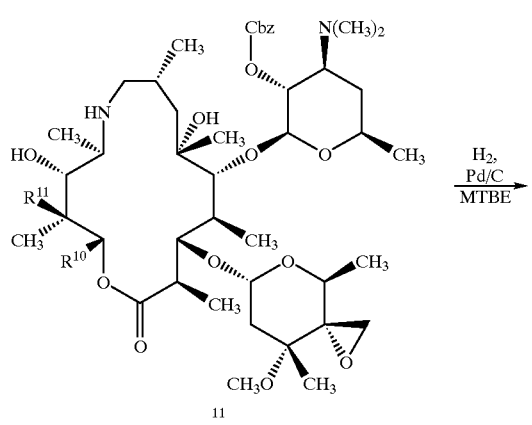

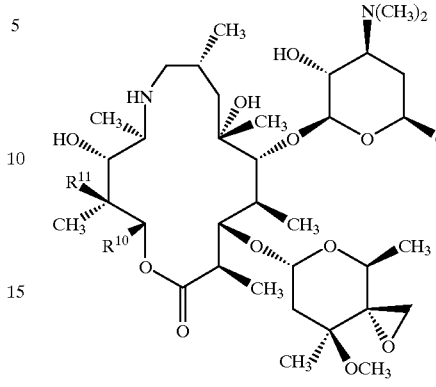

The compounds of the present invention are readily prepared. Referring to Scheme 1 above, starting compounds of formula 6 are readily available, either commercially or via conventional organic synthesis. A preferred compound of formula 6 is erythromycin A($R^{10}$=ethyl; $R^{11}$=—OH). The compounds of formula 6 are converted to compounds of formula 5 wherein $R^{11}$=cladinosyl by known means, such as are described in U.S. Pat. Nos. 4,474,768 and 4,517,350. In general, the compounds of formula 6 are treated with hydroxylamine in the presence of base, preferably an inorganic base such as an alkali metal bicarbonate or carbonate, or an alkaline earth carbonate, in the presence of water and a water-soluble organic solvent, to afford the oxime compounds of formula 7. A preferred compound of formula 7 is that in which $R^{10}$=ethyl, and $R^{11}$=OH. Preferably, the inorganic base is sodium carbonate, and the water-soluble organic solvent is methanol. The compounds of formula 7 are then treated with aqueous base and a reagent that converts the oxime hydroxyl group of the compounds of formula 7 into a leaving group, and ultimately provides the iminoether compounds of formula 8. Reagents useful in this regard include, but are not limited to, p-toluenesulfonyl halides or anhydrides, methanesulfonyl halides or anhydrides, trifluoromethanesulfonyl halides or anhydrides, p-bromobenzenesulfonyl halides or anhydrides, and the like. Preferably, the reagent is p-toluenesulfonyl chloride. A preferred compound of formula 8 is that in which $R^{10}$=ethyl, and $R^{11}$=—OH. The compounds of formula 8 are then reduced with a conventional hydride reducing agent, preferably sodium borohydride, to afford the compounds of formula 5 wherein $R^9$ is cladinosyl. In a preferred embodiment, the compound of formula 5 is desmethylazithromycin.

Compounds of formula 5 are converted to compounds of formula 1 by methods herein described. It will be understood by those skilled in the art that the compounds of formula 5 are converted to the compounds of formula 1 wherein $R^1$ is trans with respect to the methyl group at position 11 of formula 1, and is

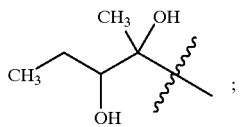

$R^2$=methyl; $R^6$, $R^7$, and $R^8$=hydrogen; and $R^9$=cladinosyl. The compounds of formula 1 wherein $R^1$=

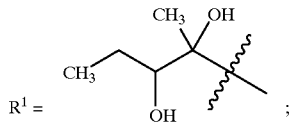

$R^2$=methyl; $R^6$, $R^7$ and $R^8$=hydrogen; and $R^9$=cladinosyl can then be converted to other compounds of formula 1, and to the compounds of formula 2, via conventional organic synthesis and via the methods described herein.

Compounds of formula 5 are converted to compounds of formula 15 by methods herein described. It will be understood by those skilled in the art that the compounds of formula 5 are converted to the compounds of formula 15 wherein $R^1$ is trans with respect to the methyl group at position 11 of formula 15, and is

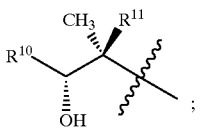

$R^2$=methyl; $R^6$, $R^7$ and $R^8$=hydrogen; and $R^9$=cladinosyl. The compounds of formula 15 wherein $R^1$=

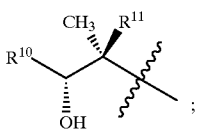

$R^2$=methyl; $R^6$, $R^7$ and $R^8$=hydrogen; and $R^9$=cladinosyl can then be converted to other compounds of formula 15, and to the compounds of formula 2, via conventional organic synthesis and via the methods described herein.

It will be understood by those skilled in the art that in addition to the compounds of formula 6, other 14-membered macrolides susceptible to a Beckman-type ring expansion, such as for example, erythromycin B, erythromycin C and clarithromycin, can be converted into precursors of 13-membered azalides contemplated by the present invention.

Where it is desired that the compounds of formula 1 are those wherein $R^9$=4"-(($R^{13}$)($R^{14}$)NCH$_2$)cladinosyl, the methods summarized in Scheme 2 can be employed.

For example, the 2' hydroxyl group of the desosaminyl group of the compounds of formula 5 can first be protected with a suitable protecting group, preferably with a benzyloxycarbonyl ("Cbz") group using Cbz-Cl, to afford the compounds of formula 9. Such a reaction can be performed at a temperature of about −78° C. to about room temperature, preferably at about 0° C. A preferred compound of formula 9 is that in which $R^{10}$=ethyl, and $R^{11}$=—OH. The 4" hydroxyl group of the cladinosyl group of the compounds of formula 9 can then be oxidized using standard oxidation conditions to afford the compounds of formula 10, which bear a 4"-oxocladinosyl group. A preferred compound of formula 10 is that in which $R^{10}$=ethyl, and $R^{11}$=—H. Such oxidation conditions can be found, for example, in the Journal of Antibiotics, 1988, pages 1029–1047. Typical reaction conditions for the oxidation include: (a) Moffatt oxidation which employs N-ethyl-N'-(N,N-dimethylaminopropyl)carbodiimide and DMSO in the presence of pyridinium trifluoroacetate; or (b) Swern oxidation in which oxalyl chloride and DMSO in CH$_2$Cl$_2$ is followed by the addition of triethylamine or alternatively trifluoracetic anhydride and DMSO in CH$_2$Cl$_{12}$ is followed by the addition of triethylamine. Preferably, the oxidation is a Swern oxidation that is performed in the presence of trifluoroacetic anhydride, at a temperature of about −78° C. to about 0° C. More preferably, the Swern oxidation is performed at about −60° C.

The carbonyl group of the 4"-oxocladinosyl group of the compounds of formula 10 is then converted into an epoxide, to afford the compounds of formula 11. A preferred compound of formula 11 is that in which $R^{10}$=ethyl, and $R^{11}$=—OH. The compounds of formula 10 may be converted to the compounds of formula 11 by at least two methods. In one method (Method A), the compound of formula 10 is treated with (CH$_3$)$_3$S(O)X$^2$, wherein X$^2$ is halo, —BF$_4$ or —PF$_6$, preferably iodo, in the presence of a base such as potassium tert-butoxide, sodium tert-butoxide, sodium ethoxide, sodium hydride, 1,1,3,3-tetramethylguanidine, 1,8-diazabicyclo[5.4.0]undec-7-ene, 1,5-diazabicylo[4.3.0]non-5-ene, potassium ethoxide, or sodium methoxide, preferably a sodium-containing base such as sodium hydride, in a solvent such as THF, an ether solvent, dimethylformamide (DMF), or methyl sulfoxide (DMSO), or a mixture of two or more of the foregoing solvents, at a temperature within the range of about 0° C. to about 60° C.; alternatively, with trimethylsulfonium bromide and a strong base, such as potassium tert-butoxide, in the presence of CH$_2$Cl$_2$/THF.

In a second method (Method B), the compounds of formula 10 are treated with (CH$_3$)$_3$SX$^2$, wherein X$^2$ is halo, —BF$_4$ or —PF$_6$, preferably —BF$_4$, in the presence of a base such as potassium tert-butoxide, sodium ethoxide, sodium tert-butoxide, sodium hydride, 1,1,3,3-tetramethylguanidine, 1,8-diazabicyclo[5.4.0]undec-7-ene, 1,5-diazabicylo[4.3.0]non-5-ene, potassium ethoxide, potassium hexamethyldisilazane (KHMDS) or sodium methoxide, preferably KHMDS, in a solvent such as THF, an ether solvent, DMF, or DMSO, or a mixture of two or more of the foregoing solvents, at a temperature within the range of about −78° C. to about 60° C.

Preferably, Method B is employed, wherein trimethylsulfonium bromide and potassium tert-butoxide are used.

The protecting, preferably Cbz, group of the desosaminyl group of the compounds of formula 11 is hydrogenolyzed in the presence of H$_2$, Pd/C and any suitable organic solvent, preferably methyl tert-butyl ether ("MTBE"), to afford the compounds of formula 12. A preferred compound of formula 12 is that in which $R^{10}$=ethyl, and $R^{11}$=—OH. Lastly, the epoxide group at the 4" position of the cladinose sugar of the compounds of formula 12 is ring-opened using HN($R^{13}$)($R^{14}$), preferably in the presence of potassium iodide, to provide the compounds of formula 5, wherein $R^9$=4"-(($R^{13}$)

($R^{14}$)NCH$_2$)cladinosyl. Compounds of the formula HN($R^{13}$) ($R^{14}$) include primary and secondary alkyl, alkenyl and alkynyl amines, and are readily obtainable by those skilled in the art. Such a reaction advantageously proceeds at a temperature of about room temperature to about 80° C., preferably at about 30° C. to about 60° C. The compounds of formula 5, wherein $R^9$=4"-(($R^{13}$)($R^{14}$)NCH$_2$)cladinosyl can be converted to compounds of formulae 1 and 15 using the methods disclosed herein.

It is to be pointed out that the conversion of the compounds of formula 11 to the compounds of formula 5 wherein $R^9$=4"-(($R^{13}$)($R^{14}$)NCH$_2$)cladinosyl can be accomplished in one step by treating the compounds of formula 10 with HN($R^{13}$)($R^{14}$) in the presence of methanol, which removes the protecting group from the desosaminyl group of the compounds of formula 10. Preferably, such a reaction is performed in the presence of potassium iodide.

In order to obtain the compounds of formula 5 wherein $R^9$=4"-oxocladinose, the protecting, preferably Cbz, group that resides on the 2'-hydroxyl group of the desosaminyl group of the compounds of formula 10 is simply removed. Procedures for removing such protecting groups can be found, for example, in Greene et al., supra.

Surprisingly and unexpectedly, the present inventors have discovered that the compounds of formula 5, which are 15-membered azalides, are convertible to the compounds of formulae 1 and 15, which are 13-membered azalides.

The present inventors have discovered that the conversion of the compounds of formula 5 to the compounds of formulae 1 and 15, preferably wherein $R^6$, $R^7$ and $R^8$ are hydrogen, and preferably wherein $R^1$ is trans with respect to the methyl group at position 11 of formulae 1 and 15, can be effected by contacting a compound of the formula 5 with an acid or base.

Acids useful in this regard include, but are not limited to, inorganic acids, such as hydrochloric, hydrobromic, hydroiodic, hydrofluoric, sulfuric and nitric acids; and organic acids, such as formic, acetic, trifluoroacetic, methanesulfonic, trifluoromethanesulfonic, benzenesulfonic and p-toluenesulfonic acids. The inorganic acids are preferably used in the form of their aqueous solutions; more preferably, the inorganic acids are used in the form of their dilute, e.g., <2M, aqueous solutions. The organic acids can be used in the form of dilute aqueous or organic solutions, wherein the organic solution comprises a solvent that sufficiently solvates both the organic acid and the compound of formula 5.

Bases useful in this regard include inorganic bases, such as hydroxides of sodium, lithium, potassium, magnesium or calcium; carbonates and bicarbonates of sodium, lithium or potassium; and carbonates of magnesium or calcium bicarbonate or carbonate. Also useful are organic bases, such as triethylamine, ethyldiisopropylamine, pyridine, 4-dimethylaminopyridine, collidine, lutidine, and mixtures thereof. Preferably, the inorganic bases are used in the form of dilute aqueous solutions. Preferably the organic bases are used in the form of dilute organic solutions. Inorganic or organic bases are preferred over inorganic or organic acids.

The compounds of formula 5 can be added to the acid or base, or vice versa. Either way, the reaction of the compounds of formula 5 with the acid or base is facilitated by heating a mixture of a compound of formula 5 and an acid or base at a temperature of about room temperature to about 100° C., preferably at a temperature of about room temperature to about 60° C., and more preferably at a temperature of about 30° C. to about 40° C. Such heating can occur for a period of about 20 minutes to about 48 h, preferably for a period of about 1 hour to about 36 h.

The present invention further relates to a method of preparing a compound of formulae 1 and 15, or a pharmaceutically acceptable salt thereof, which comprises the step of heating a compound of formula 5 in the presence of solvent.

Such heating is achieved at a temperature of about room temperature to about 100° C., preferably at a temperature of about room temperature to about 60° C., and more preferably at a temperature of about 30° C. to about 40° C. The heating can occur for a period of about 20 minutes to about 48 h, preferably for a period of about 1 h to about 36 h.

Useful solvents are those that sufficiently solvate the compounds of formula 5, and include, but are not limited to, lower alkanols, diethyl ether, acetone, acetonitrile, tetrahydrofuran, ethyl acetate, benzene, toluene, chloroform, metheylene chloride, dimethylformamide, dimethylsulfoxide, N-methylpyrrolidinone, and the like, and mixtures thereof.

However, the present inventors have found that surprisingly and unexpectedly, the conversion of compounds of formula 5 to compounds of formulae 1 and 15 proceeds most rapidly in a solvent system that comprises a protic solvent. Useful protic solvents include, but are not limited to, lower alkanols, such as methanol, ethanol, n-propanol, iso-propanol, n-butanol, iso-butanol and sec-butanol; phenolic compounds, such as phenol, halophenols, naphthols and the like; water; and mixtures thereof. It is to be pointed out, however, that the protic solvent is not a carboxylic acid.

Where the solvent system comprises a protic solvent, the protic solvent is present in an amount of about 10% to about 75% by volume, preferably in an amount of about 25% to about 60% by volume.

It will be understood by those skilled in the art that the protic solvent will be miscible in the solvent in which the compound of formula 5 is heated, when heated at the heating temperature.

Preferably, the solvent system comprises acetonitrile. More preferably, the solvent system further comprises a lower alkanol or water. Where the solvent system comprises a lower alkanol, the lower alkanol is preferably methanol.

The compounds of formulae 1 and 15 can be isolated or purified via standard means, e.g., recrystallization; chromatography using a column, preparative plate or CHROMA-TOTRON® device; or by other means know to those skilled in the art. Where chromatography is employed to isolate or purify the compounds of formulae 1 and 15, the present inventors have discovered that an eluent system that comprises a hydrocarbon solvent and an organic amine provides enhanced separation results, relative to other eluent systems. Hydrocarbon solvents useful in this regard include, but are not limited to, pentane, hexane or hexanes, heptane, petroleum ether, benzene, toluene, xylenes, and the like. Preferably, the hydrocarbon solvent is hexane or hexanes. Useful organic amines include, but are not limited to, diethylamine, triethylamine, ethyldiisopropylamine, pyridine, 4-dimethylaminopyridine, collidine, lutidine, and mixtures thereof. Preferably, the organic amine is diethylamine.

Advantageously, the eluent system that comprises a hydrocarbon solvent and an organic amine further comprises a polar organic solvent. The present inventors have discovered that the addition of the polar organic solvent to the eluent system provides a better separation of the compounds of formulae 1 and 15 from other compounds, relative to an eluent system that does not comprise a polar organic solvent. Useful polar organic solvents include, but are not limited to, lower alkanols, acetonitrile, dimethylformamide, dimethylsulfoxide, N-methylpyrrolidinone, 1,4-dioxane, tetrahydrofuran, diethyl ether, ethyl acetate, and the like. Preferably, the polar organic solvent is acetonitrile. More preferably, the eluent system comprises hexanes, diethylamine and acetonitrile.

The proportions of hydrocarbon solvent, organic amine, and optionally polar organic solvent can vary, but generally, the ratio of hydrocarbon solvent to organic amine will range from about 10:1 to about 1:1, preferably about 7:1 to about 2:1. Where the eluent system further comprises a polar organic solvent, the eluent system will contain the polar organic solvent at between about 1% to about 15% by volume, preferably at between about 1.5% to about 10% by volume.

In another embodiment of the invention, preferred compounds of formulae 1 and 15 are those wherein $R^1$ is acetyl. Especially preferred are compounds of formula 1 in which $R^1$ acetyl, $R^6$, $R^7$ and $R^8$ are hydrogen, and $R^9$=cladinosyl ("Compound 1B", Table 1); and in which $R^1$=acetyl, $R^6$=methyl, $R^7$ and $R^8$ are hydrogen, and $R^9$ is cladinosyl ("Compound 1E", Table 1).

In addition to being useful as antibacterial and antiprotozoa agents, the compounds of formulae 1 and 15 wherein $R^1$ is acetyl are useful as intermediates for obtaining other compounds of formulae 1 and 15, as described below.

In general, compounds of formulae 1 and 15 wherein $R^1$ is acetyl are obtained by oxidizing compounds of formulae 1 and 15 wherein

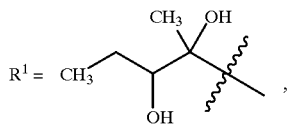

which can be obtained by the methods discussed herein. The oxidation reaction proceeds in the presence of lead tetraacetate, sodium periodate, or any other oxidizing agents that convert 1-methyl-1,2-diols to methyl ketones. Reaction conditions useful for oxidizing a 1-methyl-1,2-diol to a methyl ketone are known to those skilled in the art. Preferably, the oxidation reaction proceeds in the presence of about 1.0 to about 1.5 equivalents of lead tetraacetate per equivalent of the compound of formulae 1 and 15, and at the temperature of about −78° C. to room temperature, preferably at about −10° C. to about 10° C., and for a duration of about 10 minutes to about 6 h.

The compounds of formulae 1 and 15 wherein $R^1$=acetyl can be converted to the compounds of formulae 1 and 15 wherein $R^1$=3-N,N-dimethylamino-2-propenoyl. Such a reaction advantageously proceeds in the presence of an excess of dimethylformamide dimethyl acetal. Preferably, this reaction is performed in the absence of additional solvent.

The compounds of formulae 1 and 15 wherein $R^1$=3-N,N-dimethylamino-2-propenoyl can be converted to the compounds of formulae 1 and 15 wherein $R^1$=1-N-substituted-3-pyrazolyl by treating the compounds of formula 1 wherein $R^1$=3-N,N-dimethylamino-2-propenoyl with about 1 to about 10 equivalents of a 1-substituted hydrazine, or acid salt thereof. If an acid salt of a 1-substituted hydrazine is used, then the reaction mixture containing the acid salt and the compound of formulae 1 and 15 preferably also contains a weak organic, or alkali metal, base to buffer the reaction mixture. Preferable organic bases include diisopropylethylamine, pyridine, 4-dimethylaminopyridine, lutidine, collidine, and the like, and mixtures thereof.

Preferably, the organic base is diisopropylethylamine. The reaction between the compounds of formulae 1 and 15 wherein $R^1$=3-N,N-dimethylamino-2-propenoyl and the 1-substituted hydrazine or its acid salt, proceeds in a protic solvent, such as one described above, at a temperature ranging from about 50° C. to about 115° C., for a duration of about 1 h to about 5 days. Preferably, the protic solvent is 2-methoxyethanol or 2-propanol.

The compounds of formulae 1 and 15 wherein $R^1$=3-N,N-dimethylamino-2-propenoyl can be converted to the compounds of formaulae 1 and 15 wherein $R^1$=

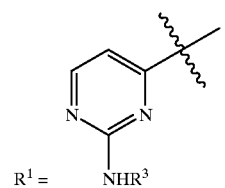

according to the procedure used to obtain the compounds of formulae 1 and 15 wherein $R^1$=1-N-substituted-3-pyrazolyl, except that $R^3N(H)C(=NH)NH_2$ is used in place at the 1-substituted hydrazine. Methods for obtaining $R^3N(H)C(=NH)NH_2$ are known to those skilled in the art.

The compounds of formulae 1 and 15 wherein $R^1$=3-N,N-dimethylamino-2-propenoyl can be converted to the compounds of formaulae 1 and 15 wherein $R^1$=

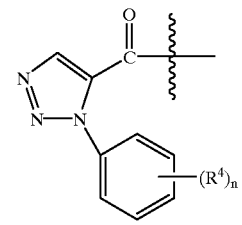

by reacting the compound of formulae 1 and 15 wherein $R^1$=3-N,N-dimethylamino-2-propenoyl with

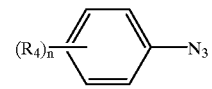

in an aprotic solvent at a temperature ranging from about 50° C. to about 110° C., for a duration of about 1 hour to about 5 days. Methods for obtaining

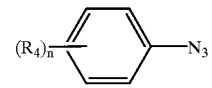

are known to those skilled in the art. Useful aprotic solvents include, but are not limited to, pentane, hexanes, heptane, toluene, benzene, xylenes, petroleum ether, tetrahydrofuran, 1,4-dioxane and the like. Preferably, the aprotic solvent is toluene.

The compounds of formulae 1 and 15 wherein $R^1$=3-N, N-dimethylamino-2-propenoyl can be converted to the compounds of formaulae 1 and 15 wherein $R^1$=3-isoxazolyl by reacting the compound of formaulae 1 and 15 wherein $R^1$=3-N,N-dimethyl-2-propenoyl with about 1 to about 10 equivalents of hydroxylamine or an acid salt thereof. The reaction used to obtain compounds of formulae 1 and 15 wherein $R^1$=3-isoxazolyl is preferably performed in an aprotic solvent, such as one described above, at a temperature at or about room temperature for a duration of about one to about five days. More preferably, the aprotic solvent is 1,4-dioxane.

The compounds of formulae 1 and 15 wherein $R^1$=acetyl can be converted into the compounds of formula 2 wherein X=—C(O)—by reacting the compound of formulae 1 and 15 wherein $R^1$=acetyl with an excess of dimethylformamide dimethyl acetal to afford the compounds of formulae 1 and 15 wherein $R^1$ is 3-N,N-dimethylamino-2-propenoyl, described above. The compounds of formulae 1 and 15 wherein $R^1$ is 3-N,N-dimethylamino-2-propenoyl are intramolecularly cyclized to provide the compounds of formula 2 wherein X=—C(O)—. Such intramolecular cyclization advantageously proceeds at high temperature, e.g., at about 110° C. or above. Accordingly, intramolecular cyclization is effected by heating a mixture of a high boiling solvent and a compound of formulae 1 and 15 wherein $R^1$ is 3-N,N-dimethylamino-2-propenoyl to a temperature of about 110° C. or above for a duration of about 6 h to about 48 h, preferably for about 12 h to about 24 h. Suitable high boiling solvents include, but are not limited to, toluene, xylenes, chlorobenzene, dimethylformamide, 2-methoxyethanol, dimethylsulfoxide and the like. Preferably, the high boiling solvent is 2-methoxyethanol.

The compounds of formula 2 wherein X=—C(O)—are converted to the compounds of formula 2 wherein X=—CH(OH)—by treating the compounds of formula 2 wherein X=—C(O)—with a hydride reducing agent such as $NaBH_4$, $LiAlH_4$, $NaAlH_4$, a SELECTIDE® reducing agent, or another hydride reagent known to those skilled in the art.

The compounds of the present invention may have asymmetric carbon atoms and therefore exist in different enantiomeric and diastereomeric forms. Diastereomeric mixtures can be separated into their individual diastereomers on the basis of their physical chemical differences by methods known to those skilled in the art, for example, by chromatography or fractional crystallization. Enantiomers may be separated by converting the enantiomeric mixtures into a diastereomeric mixture by reaction with an appropriate optically active compound (e.g., alcohol), separating the diastereomers and converting (e.g., hydrolyzing) the individual diastereomers to the corresponding pure enantiomers. The use of all such isomers, including diastereomer mixtures and pure enantiomers, are considered to be part of the present invention.

The compounds of the present invention that are basic in nature are capable of forming a wide variety of different salts with various inorganic and organic acids. Although such salts must be pharmaceutically acceptable for administration to mammals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by contacting the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired salt can also be precipitated from a solution of the free base in an organic solvent by adding to the solution an appropriate mineral or organic acid.

Those compounds of the present invention that are acidic in nature are capable of forming base salts with various cations. For compounds that are to be administered to mammals, fish or birds such salts must be pharmaceutically acceptable. Where a pharmaceutically acceptable salt is required, it may be desirable to initially isolate the compound of the present invention from the reaction mixture as a pharmaceutically unacceptable salt and then simply convert the latter to a pharmaceutically acceptable salt in a process analogous to that described above relating to the conversion of pharmaceutically unacceptable acid addition salts to pharmaceutically acceptable salts. Examples of base salts include the alkali metal or alkaline-earth metal salts and particularly the sodium, amine and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium, calcium, magnesium, various amine cations, etc. These salts can easily be prepared by contacting the corresponding acidic compounds with an aqueous solution containing the desired pharmacologically acceptable bases with cations such as sodium, potassium, calcium, magnesium, various amine cations, etc., and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The antibacterial and antiprotozoa activity of the compounds of the present invention against bacterial and protozoa pathogens is demonstrated by the compounds' ability to inhibit growth of defined strains of human or animal pathogens.

Assay I

Assay I, described below, employs conventional methodology and interpretation criteria and is designed to provide direction for chemical modifications that may lead to compounds that circumvent defined mechanisms of macrolide resistance. In Assay I, a panel of bacterial strains is assembled to include a variety of target pathogenic species, including representatives of macrolide resistance mechanisms that have been characterized. Use of this panel enables the chemical structure/activity relationship to be determined with respect to potency, spectrum of activity, and structural elements or modifications that may be necessary to obviate resistance mechanisms. Bacterial pathogens that comprise the screening panel are shown in the table below. In many cases, both the macrolide-susceptible parent strain and the macrolide-resistant strain derived from it are available to provide a more accurate assessment of the compounds' ability to circumvent the resistance mechanism. Strains that contain the gene with the designation of ermA/ermB/ermC are resistant to macrolides, lincosamides, and streptogramin B antibiotics due to modifications (methylation) of 23S rRNA molecules by an Erm methylase, thereby generally prevent the binding of all three structural classes. Two types of macrolide efflux have been described; msrA encodes a component of an efflux system in staphylococci that prevents the entry of macrolides and streptogramins while mefA/E encodes a transmembrane protein that appears to efflux only macrolides. Inactivation of macrolide antibiotics can occur and can be mediated by either a phosphorylation of the 2'-hydroxyl (mph) or by cleavage of the macrocyclic lactone (esterase). The strains may be characterized using conventional polymerase chain reaction (PCR) technology and/or by sequencing the resistance determinant. The use of PCR technology in this application is described in J. Sutcliffe et al., "Detection Of Erythromycin-Resistant Determinants By PCR", Antimicrobial Agents and Chemotherapy, 40(11), 2562–2566 (1996). The assay is performed in microtiter trays and interpreted according to *Performance Standards for Antimicrobial Disk Susceptibility Tests—Sixth Edition; Approved Standard*, published by The National Committee for Clinical Laboratory Standards (NCCLS) guidelines; the minimum inhibitory concentration (MIC) is used to compare strains. Compounds are initially dissolved in dimethylsulfoxide (DMSO) as 40 mg/ml stock solutions.

| Strain Designation | Macrolide Resistance Mechanism(s) |
|---|---|
| *Staphylococcus aureus* 1116 | susceptible parent |
| *Staphylococcus aureus* 1117 | ermB |
| *Staphylococcus aureus* 0052 | susceptible parent |
| *Staphylococcus aureus* 1120 | ermC |
| *Staphylococcus aureus* 1032 | msrA, mph, esterase |
| *Staphylococcus hemolyticus* 1006 | msrA, mph |
| *Streptococcus pyogenes* 0203 | susceptible parent |
| *Streptococcus pyogenes* 1079 | ermB |
| *Streptococcus pyogenes* 1062 | susceptible parent |
| *Streptococcus pyogenes* 1061 | ermB |
| *Streptococcus pyogenes* 1064 | ermB |
| *Streptococcus agalactiae* 1024 | susceptible parent |
| *Streptococcus agalactiae* 1023 | ermB |
| *Streptococcus pneumoniae* 1016 | susceptible |
| *Streptococcus pneumoniae* 1046 | ermB |
| *Streptococcus pneumoniae* 1095 | ermB |
| *Streptococcus pneumoniae* 1175 | mefE |
| *Streptococcus pneumoniae* 0085 | susceptible |
| *Haemophilus influenzae* 0131 | susceptible |
| *Moraxella catarrhalis* 0040 | susceptible |
| *Moraxella catarrhalis* 1055 | erythromycin intermediate resistance |
| *Escherichia coli* 0266 | susceptible |

Assay II is utilized to test for activity against *Pasteurella multocida* and Assay III is utilized to test for activity against *Pasteurella haemolytica*.

Assay II

This assay is based on the liquid dilution method in microliter format. A single colony of *P. multocida* (strain 59A067) is inoculated into 5 ml of brain heart infusion (BHI) broth. The test compounds are prepared by solubilizing 1 mg of the compound in 125 $\mu$l of dimethylsulfoxide (DMSO). Dilutions of the test compound are prepared using uninoculated BHI broth. The concentrations of the test compound used range from 200 $\mu$g/ml to 0.098 $\mu$g/ml by two-fold serial dilutions. The *P. multocida* inoculated BHI is diluted with uninoculated BHI broth to make a $10^4$ cell suspension per 200 $\mu$l. The BHI cell suspensions are mixed with respective serial dilutions of the test compound, and incubated at 37° C. for 18 hours. The minimum inhibitory concentration (MIC) is equal to the concentration of the compound exhibiting 100% inhibition of growth of *P. multocida* as determined by comparison with an uninoculated control.

Assay III

This assay is based on the agar dilution method using a Steers Replicator. Two to five colonies isolated from an agar plate are inoculated into BHI broth and incubated overnight at 37° C. with shaking (200 rpm). The next morning, 300 $\mu$l of the fully grown *P. haemolytica* preculture is inoculated into 3 ml of fresh BHI broth and is incubated at 37° C. with shaking (200 rpm). The appropriate amounts of the test compounds are dissolved in ethanol and a series of two-fold serial dilutions are prepared. Two ml of the respective serial dilution is mixed with 18 ml of molten BHI agar and solidified. When the inoculated *P. haemolytica* culture reaches 0.5 McFarland standard density, about 5 $\mu$l of the *P. haemolytica* culture is inoculated onto BHI agar plates containing the various concentrations of the test compound using a Steers Replicator and incubated for 18 hours at 37° C. Initial concentrations of the test compound range from 100–200 $\mu$g/ml. The MIC is equal to the concentration of the test compound exhibiting 100% inhibition of growth of *P. haemolytica* as determined by comparison with an uninoculated control.

Assay IV

The in vivo activity of the compounds of the present invention can be determined by conventional animal protection studies well known to those skilled in the art, usually carried out in mice.

Mice are allotted to cages (10 per cage) upon their arrival, and allowed to acclimate for a minimum of 48 hours before being used. Animals are inoculated with 0.5 ml of a $3 \times 10^3$ CFU/ml bacterial suspension (*P. multocida*) strain 59A006) intraperitoneally. Each experiment has at least 3 non-medicated control groups including one infected with 0.1× challenge dose and two infected with 1× challenge dose; a 10× challenge data group may also be used. Generally, all mice in a given study can be challenged within 30–90 minutes, especially if a repeating syringe (such as a Cornwall® syringe) is used to administer the challenge. Thirty minutes after challenging has begun, the first compound treatment is given. It may be necessary for a second person to begin compound dosing if all of the animals have not been challenged at the end of 30 minutes. The routes of administration are subcutaneous or oral doses. Subcutaneous doses are administered into the loose skin in the back of the neck whereas oral doses are given by means of a feeding needle. In both cases, a volume of 0.2 ml is used per mouse. Compounds are administered 30 minutes, 4 hours, and 24 hours after challenge. A control compound of known efficacy administered by the same route is included in each test. Animals are observed daily, and the number of survivors in each group is recorded. The *P. multocida* model monitoring continues for 96 hours (four days) post challenge.

The $PD_{50}$ is a calculated dose at which the compound tested protects 50% of a group of mice from mortality due to the bacterial infection which would be lethal in the absence of drug treatment.

The compounds of the present invention show antibacterial activity in one of the above-described assays, particularly in Assay IV.

The compounds of the present invention, and the pharmaceutically acceptable salts thereof (hereinafter "the active compounds"), may be administered through oral, parenteral, topical, or rectal routes in the treatment of bacterial and protozoal infections. In general, these compounds are most desirably administered in dosages ranging from about 0.2 mg per kg body weight per day (mg/kg/day) to about 200 mg/kg/day in single or divided doses (i.e., from 1 to 4 doses per day), although variations will necessarily occur depending upon the species, weight and condition of the subject being treated and the particular route of administration chosen. However, a dosage level that is in the range of about 4 mg/kg/day to about 50 mg/kg/day is most desirably employed. Variations may nevertheless occur depending upon the species of mammal, fish or bird being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds may be administered alone or in combination with pharmaceutically acceptable carriers or diluents by the routes previously indicated, and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the active compounds are present in such dosage forms at concentration levels ranging from about 5.0% to about 99% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active compound may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques will known to those skilled in the art.

Additionally, it is also possible to administer the active compounds of the present invention topically and this may be done by way of creams, jellies, gels, pastes, patches, ointments and the like, in accordance with standard pharmaceutical practice.

For administration to animals other than humans, such as cattle or domestic animals, the active compounds may be administered in the feed of the animals or orally as a drench composition.

The active compounds may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The active compounds may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol or polyethyleneoxide-polylysine substituted with palmitoylresidues. Furthermore, the active compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

The following Examples further illustrate the method and intermediates of the present invention. It is to be understood that the present invention is not limited to the specific details of the Examples provided below.

The compounds of Examples 1–12 have the general formula 3 below, with the $R^1$ and $R^6$ substituents indicated in Table 1, below. The compounds were prepared as described in Examples 1–12.

TABLE 1

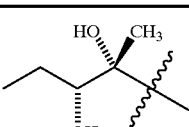

| Compound | $R^1$ | $R^6$ |
|---|---|---|
| 1A |  | hydrogen |
| 1B | acetyl | hydrogen |
| 1C | 3-N,N-dimethylamino-2-propenoyl | hydrogen |
| 1D | 3-pyrazolyl | hydrogen |
| 1E | acetyl | methyl |
| 1F | 3-N,N-dimethylamino-2-propenoyl | methyl |
| 1G | 3-pyrazolyl | methyl |
| 1H | 1-N-methyl-3-pyrazolyl | methyl |
| 1I | 1-N-benzyl-3-pyrazolyl | methyl |
| 1J | 1-N-(3-hydroxybenzyl)-3-pyrazolyl | methyl |

TABLE 1-continued

| Compound | R$^1$ | R$^6$ |
|---|---|---|
| 1K | (2-(4-fluorophenyl)-3-pyrimidinyl | methyl |
| 1L | (2-phenylamino)-3-pyrimidinyl | methyl |
| 1M | 1-N-methyl-5-pyrazolyl | methyl |

EXAMPLE 1

Compound 1A

Desmethylazithromycin (30 g, 41 mmol) was added to deionized water (2 L), and then acetonitrile was added to effect complete dissolution (total volume was approximately 4.5 L). The resulting mixture was allowed to stir at ambient temperature for 2 days, at which time HPLC indicated the presence of a new peak (approx. 22% by peak area). The acetonitrile was removed in vacuo. To the resulting residue was added potassium carbonate (30 g), followed by methylene chloride (0.3 L). The mixture was shaken, and the lower organic phase removed. The aqueous phase was re-extracted with methylene chloride (2×0.3 L). Combined organic phases were dried over sodium sulfate, and then concentrated in vacuo to afford a dry foam (30 g), which was purified on a slurry-packed silica gel column using 5/1/0.5 (v/v/v) hexanes-diethylamine-acetonitrile. During the separation, the solvent system was switched to 4/1/0.1, and, finally, 3/1.5/0.5 hexanes-diethylamine-acetonitrile. Concentration of the appropriate, late-running fractions afforded Compound 1A as a dry foam.

EXAMPLE 2

Compound 1B

To a solution of Compound 1A (7.63 g, 10.41 mMole) in methylene chloride (100 mL) at 0° C. was added in one portion lead(IV) acetate (5.54 g, 12.49 mMole). The resulting mixture was stirred for 30 minutes at 0° C. and then quenched with a saturated solution of aqueous sodium bicarbonate (100 mL). The mixture was transferred to a separatory funnel and the methylene chloride layer was removed. The aqueous layer was extracted with methylene chloride (2×50 mL). The combined methylene chloride fractions were washed with brine (50 mL), dried over magnesium sulfate, filtered and concentrated under reduced pressure. The residue was purified by flash chromatography on silica gel eluting with 0.2% ammonium hydroxide (10% aqueous)/5% methanol/94.8% methylene chloride to afford Compound 1B (5.64 g, 8.43 mMole) as a white solid.

EXAMPLE 3

Compound 1C

Compound 1B (100 mg, 0.15 mMole) was dissolved in dimethylformamide dimethyl acetal (2 mL) and heated to reflux under nitrogen for 8 h. The mixture was allowed to cool to room temperature and then diluted with ethyl acetate (25 mL). The mixture was washed with water (10 mL) and brine (10 mL). The ethyl acetate solution was dried over magnesium sulfate, filtered, and then concentrated under reduced pressure. The residue was purified by flash chromatography on silica gel, eluting with 0.2% ammonium hydroxide (10% aqueous)/10% methanol/methylene chloride to provide Compound 1C (yield: 65 mg, 60%).

EXAMPLE 4

Compound 1D

Compound 1C (100 mg, 0.14 mMole) and hydrazine monohydrate (5 mL, 0.15 mmole) were dissolved in 2-methoxyethanol (1.5 mL) and heated to 105° C. under nitrogen. After 2 h the mixture was allowed to cool to room temperature, and then concentrated under reduced pressure. The residue was purified by flash chromatography on silica gel, eluting with 0.2% ammonium hydroxide (10% aqueous) l10% methanol/methylene chloride to provide Compound 1D as a white solid (yield: 58 mg, 60%).

EXAMPLE 5

Compound 1E

To a solution of Compound 1B (3.9 g, 5.8 mMole) in chloroform (58 mL) was added formic acid (330 mL, 869 mMole) and formaldehyde (37% aqueous, 1.3 mL, 17.33 mMole). The mixture was heated to 60° C. for 7 h. After cooling to room temperature, the mixture was transferred to a separatory funnel and washed with aqueous sodium bicarbonate (20 mL). The chloroform fraction was dried over magnesium sulfate, filtered and concentrated to provide Compound 1E (yield: 3.9 g, 98%), which was used without further purification.

EXAMPLE 6

Compound 1F

Compound 1E was dissolved in dimethylformamide dimethyl acetal (25 mL) and heated to reflux under nitrogen for 36 h. The mixture was allowed to cool to room temperature, and then concentrated under reduced pressure. The residue was purified by flash chromatography on silica gel, eluting with 0.2% ammonium hydroxide (10% aqueous)/8% methanol/methylene chloride to provide Compound 1F (yield: 1.36 g, 80%).

EXAMPLE 7

Compound 1G

Compound 1F (250 mg, 0.34 mMole) and hydrazine monohydrate (16 mL, 0.5 mmole) were dissolved in 2-methoxyethanol (3.4 mL) and heated to 105° C. under nitrogen. After 4 h, the mixture was allowed to cool to room temperature and then concentrated under reduced pressure. The residue was purified by flash chromatography on silica gel, eluting with 0.2% ammonium hydroxide (10% aqueous)/10% methanol/methylene chloride to provide Compound 1G as a white solid.

EXAMPLE 8

Compound 1I

Compound 1F (250 mg, 0.34 mMole), benzyl hydrazine dihydrochloride (73 mL, 0.37 mmole) and diisopropylethylamine (180 µL, 1.02 mMole) were dissolved in 2-methoxyethanol (3.5 mL) and heated to 105° C. under nitrogen. After 48 h, the mixture was allowed to cool to room temperature and then concentrated under reduced pressure. The residue was purified by flash chromatography on silica gel, eluting with 0.2% ammonium hydroxide (10% aqueous)10% methanol/methylene chloride to provide Compound 1I as a white solid (yield: 137 mg, 50%).

EXAMPLE 9

Compound 1J

Compound 1F (250 mg, 0.34 mMole), 3-hydroxybenzyl hydrazine dihydrochloride (142 mL, 0.68 mmole) and diisopropylethylamine (148 µL, 0.85 mMole) were dissolved in 2-propanol (3.5 mL) and heated to reflux under nitrogen. After 5 h, the mixture was allowed to cool to room temperature and then concentrated under reduced pressure. The residue was purified by flash chromatography on silica gel, eluting with 0.2% ammonium hydroxide (10% aqueous)/10% methanol/methylene chloride to provide Compound 1J as a white solid (yield: 147 mg, 53%).

EXAMPLE 10

Compound 1K

Compound 1F (250 mg, 0.34 mMole), 4-fluorophenyl guanidine carbonate (240 mg, 0.68 mmole) and diisopropylethylamine (148 µL, 0.85 mMole) were dissolved in 2-propanol (3.5 mL) and heated to reflux under nitrogen. After 24 h, the mixture was allowed to cool to room temperature and then concentrated under reduced pressure. The residue was purified by flash chromatography on silica gel, eluting with 0.2% acetonitrile/20% diethylamine/hexanes to provide Compound 1K as a white solid (yield: 120 mg, 42%).

EXAMPLE 11

Compound 1L

Compound 1F (125 mg, 0.168 mMole), phenyl guanidine carbonate (84 mg, 0.252 mmole) and potassium carbonate (70 mg, 0.5 mMole) were dissolved in 2-propanol (1.5 mL) and heated to reflux under nitrogen. After 48 h, the mixture was allowed to cool to room temperature and then diluted with methylene chloride (25 mL). The mixture was then washed with water (10 mL), dried over magnesium sulfate, filtered and concentrated under reduced pressure. The residue was purified by flash chromatography on silica gel, eluting with 0.2% ammonium hydroxide (10% aqueous)/10% methanol/methylene chloride to provide Compound 1L (54 mg, 40%) as a white solid.

EXAMPLE 12

Compounds 1H and 1M

Compound 1F (260 mg, 0.35 mMole) and methyl hydrazine monohydrate (56 µL, 1.05 mmole) were dissolved in 2-methoxyethanol (3.5 mL) and heated to 115° C. under nitrogen. After 6 h, the mixture was allowed to cool to room temperature and then concentrated under reduced pressure. The residue was purified by flash chromatography on silica gel, eluting with 1% acetonitrile/20% diethylamine/hexanes to provide Compound 1H (yield: 42 mg, 17%) and Compound 1M (yield: 21 mg, 8%) as white solids.

The compounds of Examples 13–14 have the general formula 4 below, with the X substituents indicated in Table 2, below. The compounds were prepared as described in Examples 13–14.

TABLE 2

| Compound | X |
| --- | --- |
| 2A | —C(O)— |
| 2B | —CH(OH)— |

EXAMPLE 13

Compounds 2A and 1C

Compound 1B (1.5 g, 2.23 mMole) was dissolved in dimethylformamide dimethyl acetal (15 mL) and heated to 105° C. for 16 h. After cooling to room temperature, the mixture was concentrated under reduced pressure. The residue was dissolved in 2-methoxyethanol (25 mL) and heated to 125° C. for 16 h. The mixture was allowed to cool to room temperature and then diluted with ethyl acetate (100 mL). The mixture was washed with water (2×20 mL) and brine (20 mL), dried over magnesium sulfate, filtered, and concentrated under reduced pressure. The residue was purified by flash chromatography on silica gel, eluting with 0.2% ammonium hydroxide (10% aqueous)/10% methanol/methylene chloride to provide Compounds2A (yield: 221 mg, 15%) and 1C (833 mg, 54%).

EXAMPLE 14

Compound 2B

To a solution of Compound 2A (150 mg, 0.21 mMole) in ethanol (2 mL) at 0° C. was added in one portion sodium borohydride (33 mg, 0.84 mMole). The mixture was stirred at 0° C. for 2 h and then poured slowly into water (25 mL). The mixture was transferred to a separatory funnel and extracted methylene chloride (3×20 mL). The combined methylene chloride fractions were dried over magnesium sulfate, filtered and concentrated. The residue was purified by flash chromatography on silica gel eluting with 0.2% ammonium hydroxide (10% aqueous)/5% methanol/methylene chloride to afford Compound 2B (yield: 103 mg, 71%) as a white solid.

The compounds of Examples 15–17 have the general formula 14 below, with the $R^1$ substituents indicated in Table 3, below. The compounds were prepared as described in Examples 15–17.

TABLE 3

| Compound | R¹ |
|---|---|
| 1N | (structure: CH₃, CH₃, OH, OH fragment) |
| 1O | (structure: cyclic carbonate with CH₃ and ethyl) |

EXAMPLE 15

Compound 1N (Method A)

To a 2 L erlenmeyer flask was added desmethylazithromycin (190.5 g, 259.2 mmol), methylene chloride (572 mL), and magnesium sulfate (38 g). The mixture was stirred for 10 min then filtered into a 5 L round bottom flask. Additional methylene chloride (2285 mL) was added and the solution cooled to 0–5° C. CBZ-Cl (58.4 mL) was then added over 10 min. The reaction stirred at ~0° C. for 6 hrs then at ambient temperature overnight. HPLC analysis indicated the presence of residual starting material such that the reaction was re-cooled to ~0° C. and additional CBZ-Cl (19.5 mL) was added in a single portion. The reaction stirred for 5.5 hrs at 0° C. then for 2.5 hrs at ambient temperature. TLC indicated a complete reaction. The reaction was quenched with saturated aqueous sodium bicarbonate (953 mL) and the phases separated. The organic phase was dried over magnesium sulfate, then filtered and concentrated to afford the compound of formula 9 wherein $R^{10}$=ethyl, and $R^{11}$=—OH.

To a 5 L round bottom flask containing the compound of formula 9 wherein $R^{10}$=ethyl, and $R^{11}$=—OH (225.3 g) in methylene chloride (901 mL) and DMSO (450 mL) at −65° C. was added trifluoroacetic anhydride (82.4 mL). The temperature was maintained at ~60° C. throughout the addition which was complete in 9 min. The reaction stirred at −65 to −70° C. for 20 min. The reaction was quenched with triethylamine (145 mL) then stirred at −60° to −65° C. for 20 min. To the reaction mixture was then added water (1127 mL) over 3 min, at which point the temperature rose to −2° C. The reaction mixture was stirred for 10 min and the phases were allowed to separate. The organic phase was washed with water, (675 mL) then with saturated aqueous sodium chloride (675 mL). The organic phase was dried over magnesium sulfate then filtered and organic solvents removed by distillation. MTBE was added and distilled to remove all traces of methylene chloride and DMSO. Additional MTBE was added to a total volume of 3380 mL. Dibenzoyl-D-tartaric acid monohydrate (87.8 g) in MTBE (1126 mL) was added to form a thick slurry. The mixture was heated to reflux and stirred overnight. After cooling to ambient temperature, the solids were collected on a Buchner funnel and rinsed with MTBE. The solids were dried in a drying oven at 40° C. to afford 258.3 g of the dibenzoyl tartrate salt of the compound formula 10 wherein $R^{10}$=ethyl, and $R^{11}$=—OH.

To a 3 L round bottom flask was added methylene chloride (800 mL) and the dibenzoyl tartrate salt of the compound of formula 10 wherein $R^{11}$=ethyl, and $R^{11}$=—OH (188 g). Water (400 mL) and potassium carbonate (45.5 g) were added and the mixture stirred at ambient temperature for 5 min. The organic phase was separated, then washed with water (250 mL) and dried over magnesium sulfate. Drying agent was removed by filtration, and the resultant solution evaporated under a stream of nitrogen to a final volume of 623 mL to afford a free-base ketone.

To a 5 L round bottom flask was added THF (623 mL) and trimethylsulfonium bromide (74.7 g). The resultant slurry was cooled to −10° C. and potassium tert-butoxide (54.4 g) added. The reaction mixture was stirred for 10 min at −10° C. then cooled to −70° C. over 5 min. A solution of the free-base ketone was added over 11 min, keeping the temperature between −60 and −65° C. HPLC indicated the reaction was complete after 90 min. The reaction was quenched at −60° C. using a solution of ammonium chloride (315 g) in water (1800 mL). The temperature rose to −5° C. during the quench. The reaction mixture was warmed to 5–10° C., and the phases separated. The organic phase was dried over sodium sulfate then filtered and concentrated to afford the compound of formula 11 wherein $R^{10}$=ethyl, and $R^{11}$=—OH, (117.4 g) as a yellow foam. HPLC indicated a purity of 61.4% by peak area.

To a solution of the compound of formula 11 wherein $R^{10}$=ethyl and $R^{11}$=—OH (275 g, 312 mmol) in dry methanol (2.75 L) was added potassium iodide (518 g, 3.12 mol) and n-propylamine (250 mL, 3.04 mol). The mixture was stirred overnight at 45° C. TLC indicated a complete reaction. The reaction was concentrated on a rotary evaporator and the residue partitioned between water (2.5 L) and methylene chloride (2.5 L). The pH of the aqueous phase was adjusted to 6.7 using 3N aqueous HCl. The extraction was repeated one additional time. Combined aqueous phases were combined with fresh methylene chloride (1.5 L) and the pH of the aqueous phase adjusted to 8.5 using solid potassium carbonate. The phases were separated and the aqueous phase re-extracted twice with additional methylene chloride. Combined organic phases were dried over sodium sulfate, then filtered. The filtrate was concentrated on a rotary evaporator to afford a beige foam (230 g). Purification of the foam was effected on a slurry-packed silica gel column using 19/3 (v/v) hexanes-diethylamine as the mobile phase. In this manner, 125 g of crude product afforded 72 g of the compound of formula 5, wherein $R^9$=4''-(propylaminomethyl)cladinosyl, $R^{10}$=ethyl, and $R^{11}$=—OH, as a white, amorphous foam.

The compound of formula 5 wherein $R^9$=4''-(propylaminomethyl)cladinosyl, $R^{10}$=ethyl, and $R^{11}$=—OH (10 g, 12.4 mmol), was dissolved in acetonitrile (0.5 L) at ambient temperature. Deionized water (1 L) was then added, which caused precipitation. Additional acetonitrile (0.5 L) was then added to afford a homogenous solution which was stirred at ambient temperature for 30 hrs. HPLC analysis indicated the formation of a new component that comprised ~20% total peak area.

Organic solvent was removed on a rotary evaporator. Potassium carbonate (30 g) was added to the aqueous residue followed by methylene chloride (0.3 L). The mixture was shaken and the lower organic phase removed. Two additional extractions (2×0.3 L) were also performed. Combined organic phases were dried over sodium sulfate, then filtered and the resultant solution concentrated to a dry foam (~10 g).

The resultant mixture of the compound of formula 5 wherein, $R^9$=4"-(propylaminomethyl)cladinosyl, $R^{10}$=ethyl, and $R^{11}$=—OH; and Compound 1N, was dissolved in a mixture of methylene chloride and 193 (v/v) hexanes-diethylamine, and placed on a slurry-packed silica gel column, then eluted with the 19/3 system. The eluant was switched to 19/6 hexanes-diethylamine in fraction 56. Fraction 9–17 were combined and concentrated to a dry foam which contained only unreacted starting material. Fractions 52–72 were combined and concentrated, and contained Compound 1N (79% purity by HPLC).

EXAMPLE 16

Compound 1N (Method B)

The compound of formula 5 wherein $R^9$=4"-(propylaminomethyl)cladinosyl, $R^{10}$=ethyl, and $R^{11}$=—OH, was weighed into 6 vials (25 mg/vial). Solvents (0.5 mL per) were added as indicated below:

| Vial | Solvent |
|---|---|
| A | 2-propanol |
| B | acetonitrile |
| C | acetonitrile (0.35 mL)/water (0.35.mL) |
| D | acetone |
| E | methanol |
| F | benzene |

All vials were then heated to 50° C. in an oil-bath for 5 hrs. TLC analysis using 6/1/0.1 (v/v/v) hexanes-diethylamine-acetonitrile) indicated the presence of Compound 1N in all vials. The greatest proportion, however, was in vials C and E which contained protic solvents.

EXAMPLE 17

Compound 1O

A mixture of the compound of formula 5 wherein $R^9$=4"-(propylaminomethyl)cladinosyl, $R^{10}$= ethyl, and $R^{11}$=—OH; and Compound 1N (~15%)(0.8 g, 0.1 mmol) was dissolved in ethyl acetate (30 ml). Potassium carbonate (0.14 g, 1 mmol) and ethylene carbonate (0.5 g, 5.67 mmol) were then added, and the mixture heated to reflux under nitrogen overnight. TLC analysis using 19/3 (v/v) hexanes-diethylamine indicated the absence of both starting materials.

The reaction mixture was then filtered, and the filtrate concentrated to afford a dark oil which was purified under nitrogen on a 4 mm CHROMATOTRON® (Harrison Research, Palo Alto, Calif.) plate using (19/3 (v/v) hexanes-diethylamine as the eluant. Fractions 8–13 were combined and concentrated; NMR analysis indicated that this product corresponded to the 11,12-cyclic carbonate of the starting material. Fractions 18–39 contained a less-mobile component that was re-purified on a 2 mm plate using 3/1 (v/v) hexanes-diethylamine. Enriched fractions (16–23) were combined and re-run on a 1 mm plate in the above system to afford Compound 10 in fraction 20 (30 mg). TLC and HPLC indicated that the material was highly pure.

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

What is claimed is:

1. A compound of the formula 1

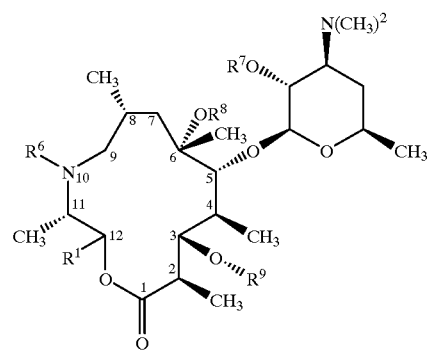

or a pharmaceutically acceptable salt thereof, wherein:

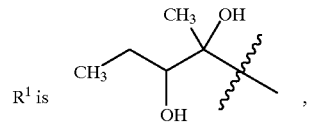

acetyl, 3-N,N-dimethylamino-2-propenoyl,

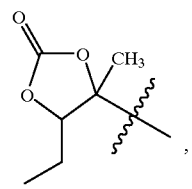

1-N-methyl-5-pyrazolyl, 3-pyrazolyl, 1-methyl-N-3-pyrazolyl, 1-N-benzyl-3-pyrazolyl, 1-N-(-3-hydroxybenzyl)-3-pyrazolyl, 3-isoxazolyl,

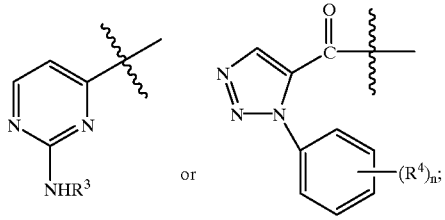

$R^2$ is hydrogen or $C_1$–$C_4$ alkyl;
$R^3$ is hydrogen, $C_1$–$C_{10}$ alkyl, $C_2$–$C_{10}$ alkenyl, $C_2$–$C_{10}$ alkynyl, —(CH$_2$)$_m$(C$_6$–C$_{10}$ aryl), or —(CH$_2$)$_m$(C$_6$–C$_{10}$ heterocyclic), each, other than hydrogen, being optionally substituted with 1 to 3 substituents independently selected from the group consisting of halogen, cyano, nitro, trifluoromethyl, azido, —C(O)$C_1$–$C_{10}$ alkyl, —C(O)$C_2$–$C_{10}$ alkenyl, —C(O)$C_2$–$C_{10}$ alkynyl, —OC(O)$C_1$–$C_{10}$ alkyl, —OC(O)$C_2$–$C_{10}$ alkenyl, —OC(O)$C_2$–$C_{10}$ alkynyl, —N(hydrogen, $C_1$–$C_{10}$ alkyl, $C_2$–$C_{10}$ alkenyl or $C_2$–$C_{10}$ alkynyl)C(O)($C_1$–$C_{10}$ alkyl, $C_2$–$C_{10}$ alkenyl or $C_2$–$C_{10}$ alkynyl), —C(O)N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), —N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), $C_1$–$C_{10}$ alkoxy, $C_6$–$C_{10}$ aryl, 5–10 membered heterocyclic, hydroxyl, methoxyl, $C_1$–$C_{10}$ alkyl, $C_2$–$C_{10}$ alkenyl, $C_2$–$C_{10}$ alkynyl, 2-pyridyl, 3-pyridyl, 4-pyridyl, 2-pyrimidyl, 4-pyrimidyl, 2-pyridylmethyl, 3-pyridylmethyl, 4-pyridylmethyl, 2-pyridylethyl, 3-pyridylethyl and 4-pyridylethyl;

m is an integer ranging from 0 to 4;

each $R^4$ is hydrogen, —$(CH_2)_m$($C_6$–$C_{10}$ aryl) or —$(CH_2)_m$($C_6$–$C_{10}$ heterocyclic), each, other than hydrogen, being optionally substituted with 1 to 3 substituents independently selected from the group consisting of halo, cyano, nitro, trifluoromethyl, azido, —C(O)$C_1$–$C_{10}$ alkyl, —C(O)$C_2$–$C_{10}$ alkenyl, —C(O)$C_2$–$C_{10}$ alkynyl, —OC(O)$C_1$–$C_{10}$ alkyl, —OC(O)$C_2$–$C_{10}$ alkenyl, —OC(O)$C_2$–$C_{10}$ alkynyl, —N(hydrogen, $C_1$–$C_{10}$ alkyl, $C_2$–$C_{10}$ alkenyl or $C_2$–$C_{10}$ alkynyl)C(O)($C_1$–$C_{10}$ alkyl, $C_2$–$C_{10}$ alkenyl or $C_2$–$C_{10}$ alkynyl), —C(O)N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), —N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), $C_1$–$C_{10}$ alkoxy, $C_6$–$C_{10}$ aryl and 5–10 membered heterocyclic;

n is an integer from 0 to 5;

$R^6$ is hydrogen or methyl;

each $R^7$ is independently hydrogen, $C_1$–$C_{20}$ alkyl, $C_2$–$C_{20}$ alkenyl, $C_2$–$C_{20}$ alkynyl, —C(O)$C_1$–$C_{20}$ alkyl, —C(O)$C_2$–$C_{20}$ alkenyl, —C(O)$C_2$–$C_{20}$ alkynyl, —C(O)N(H)$C_1$–$C_{10}$ alkyl, —C(O)N(H)$C_2$–$C_{20}$ alkenyl, —C(O)N(H)$C_2$–$C_{20}$ alkynyl, —$SO_2$(O)$C_1$–$C_{20}$ alkyl, —$SO_2$(O)$C_2$–$C_{20}$ alkenyl, —$SO_2$(O)$C_2$–$C_{20}$ alkynyl or —$PO_4^{2-}$;

$R^8$ is hydrogen or methyl;

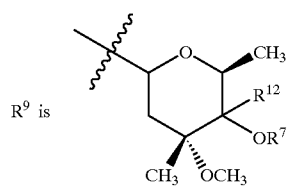

$R^9$ is or 4″-oxocladinosyl; and $R^{12}$ is $C_1$–$C_{10}$ alkyl, $C_2$–$C_{10}$ alkenyl, $C_2$–$C_{10}$ alkynyl, cyano, —$CH_2S(O)_p C_1$–$C_{10}$ alkyl, —$CH_2S(O)_p C_2$–$C_{10}$ alkenyl, —$CH_2S(O)_p C_2$–$C_{10}$ alkynyl, wherein p is an integer ranging from 0 to 2, —$CH_2O$($C_1$–$C_{10}$ alkyl), —$CH_2O$($C_2$–$C_{10}$ alkenyl), —$CH_2O$($C_2$–$C_{10}$ alkynyl), —$CH_2N$(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), —$(CH_2)_m$($C_6$–$C_{10}$ aryl) or —$(CH_2)_m$(5–10 membered heteroaryl), wherein m is an integer ranging from 0 to 4, and wherein the alkyl, alkenyl, alkynyl, aryl and heteroaryl moieties of the foregoing are optionally substituted with 1 to 3 substituents independently selected from the group consisting of halo, cyano, nitro, trifluoromethyl, azido, —C(O)$C_1$–$C_{10}$ alkyl, —C(O)$C_2$–$C_{10}$ alkenyl, —C(O)$C_2$–$C_{10}$ alkynyl, —OC(O)$C_1$–$C_{10}$ alkyl, —OC(O)$C_2$–$C_{10}$ alkenyl, —OC(O)$C_2$–$C_{10}$ alkynyl, —N(hydrogen, $C_1$–$C_{10}$ alkyl, $C_2$–$C_{10}$ alkenyl or $C_2$–$C_{10}$ alkynyl)C(O)($C_1$–$C_{10}$ alkyl, $C_2$–$C_{10}$ alkenyl or $C_2$–$C_{10}$ alkynyl), —C(O)N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), —N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), $C_{1-C10}$ alkoxy, $C_6$–$C_{10}$ aryl or 5–10 membered heterocyclic, hydroxy, $C_1$–$C_6$ alkyl, $C_1$–$C_6$ alkoxy, $C_6$–$C_{10}$ aryl and 5–10 membered heteroaryl.

2. A compound of the formula 15

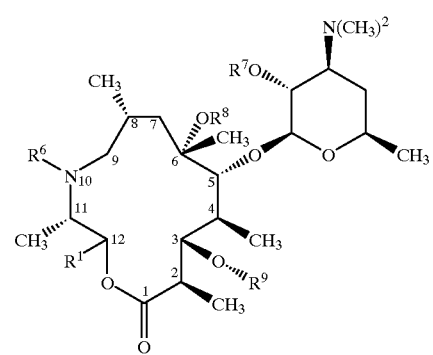

or a pharmaceutically acceptable salt thereof, wherein:

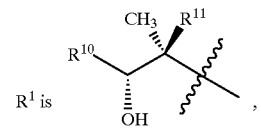

$R^1$ is acetyl, 3-N,N-dimethylamino-2-propenoyl,

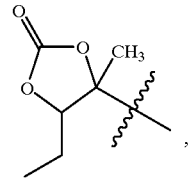

1-N-methyl-5-pyrazolyl, 3-pyrazolyl, 1-methyl-N-3-pyrazolyl, 1-N-benzyl-3-pyrazolyl, 1-N-(3-hydroxybenzyl)-3-pyrazolyl, 3-isoxazolyl,

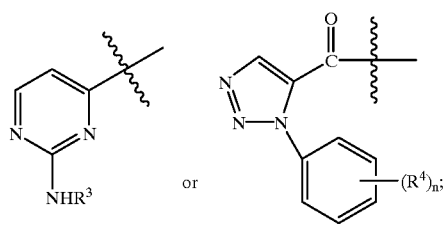

$R^9$ is

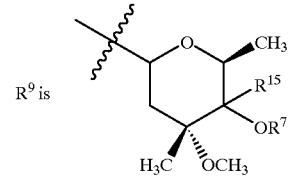

$R^2$ is hydrogen or $C_1$–$C_4$ alkyl;

$R^3$ is hydrogen, $C_1$–$C_{10}$ alkyl, $C_2$–$C_{10}$ alkenyl, $C_2$–$C_{10}$ alkynyl, —$(CH_2)_m(C_6C_{10}$ aryl), or —$(CH_2)_m(C_6$–$C_{10}$ heterocyclic), each, other than hydrogen, being optionally substituted with 1 to 3 substituents independently selected from the group consisting of the group consisting of halogen, cyano, nitro, trifluoromethyl, azido, —C(O)$C_1$–$C_{10}$ alkyl, —C(O)$C_2$–$_{10}$ alkenyl, —C(O)$C_2$–$C_{10}$ alkynyl, —OC(O)$C_1$–$C_{10}$ alkyl, —OC(O)$C_2$–$C_{10}$ alkenyl, —OC(O)$C_2$–$C_{10}$ alkynyl, —N(hydrogen, $C_1$–$C_{10}$ alkyl, $C_2$–$C_{10}$ alkenyl or $C_2$–$C_{10}$ alkynyl)C(O)($C_1$–$C_{10}$ alkyl, $C_2$–$C_{10}$ alkenyl or $C_2$–$C_{10}$ alkynyl), —C(O)N(hydrogen, $C_1$–$C_{10}$ alkyl, $C_2$–$C_{10}$ alkenyl or $C_2$–$C_{10}$ alkynyl)(hydrogen, $C_1C_{10}$ alkyl, $C_2$–$C_{10}$ alkenyl or $C_2$–$C_{10}$ alkynyl), —N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), $C_1$–$C_{10}$ alkoxy, $C_6$–$C_{10}$ aryl, 5–10 membered heterocyclic, hydroxyl, methoxyl, $C_1$–$C_{10}$ alkyl, $C_2$–$C_{10}$ alkenyl, $C_2$–$C_{10}$ alkynyl, 2-pyridyl, 3-pyridyl, 4-pyridyl, 2-pyrimidyl, 4-pyrimidyl, 2-pyrimidylmethyl, 3-pyridylmethyl, 4-pyridylmethyl, 2-pyridylethyl, 3-pyridylethyl and 4-pyridylethyl;

m is an integer ranging from 0 to 4;

each $R^4$ is hydrogen, —$(CH_2)_m(C_6$–$C_{10}$ aryl) or —$(CH_2)_m(C_6$–$C_{10}$ heterocyclic), each, other than hydrogen, being optionally substituted with 1 to 3 substituents independently selected from the group consisting of halo, cyano, nitro, trifluoromethyl, azido, —C(O)$C_1$–$C_{10}$ alkyl, —C(O)$C_2$–$C_{10}$ alkenyl, —C(O) $C_2$–$C_{10}$ alkynyl, —OC(O)$C_1$–$C_{10}$ alkyl, —OC(O) $C_2$–$C_{10}$ alkenyl, —OC(O)$C_2$–$C_{10}$ alkynyl, —N(hydrogen, $C_1$–$C_{10}$ alkyl, $C_2$–$C_{10}$ alkenyl or $C_2$–$C_{10}$ alkynyl)C(O)$C_1$–$C_{10}$ alkyl, $C_2$–$C_{10}$ alkenyl or $C_2$–$C_{10}$ alkynyl), —C(O)N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), —N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$alkynyl), $C_1$–$C_{10}$ alkoxy, $C_6$–$C_{10}$ aryl and 5–10 membered heterocyclic;

n is an integer from 0 to 5;

$R^6$ is hydrogen or methyl;

each $R^7$ is independently hydrogen, $C_1$–$C_{20}$ alkyl, $C_2$–$C_{20}$ alkenyl, $C_2$–$C_{20}$ alkynyl, —C(O)$C_1$–$C_{20}$ alkyl, —C(O)$C_2$–$C_{20}$ alkenyl, —C(O)$C_2$–$C_{20}$ alkynyl, —C(O)N(H)$C_1$–$C_{10}$ alkyl, —C(O)N(H)$C_2$–$C_{20}$ alkenyl, —C(O)N(H)$C_2$–$C_{20}$ alkynyl, —SO$_2$(O)$C_1$–$C_{20}$ alkyl, —SO$_2$(O)$C_2$–$C_{20}$ alkenyl, —SO$_2$(O)$C_2$–$C_{20}$ alkynyl or —PO$_4^{2-}$;

$R^8$ is hydrogen or methyl;

or 4"-oxocladinosyl;

$R^{10}$ is an alpha-branched $C_2$–$C_8$ alkyl, alkenyl, alkynyl, alkoxyalkyl or alkylthioalkyl group, any of which may optionally be substituted by one or more hydroxyl groups; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methyl or one or more hydroxyl, one or more $C_1$–$C_4$ alkyl groups or halo atoms; or a 3 to 6 membered oxygen or sulphur containing heterocyclic ring which may be saturated, or fully or partially unsaturated and which may optionally be substituted by one or more $C_1$–$C_4$ alkyl groups or halo atoms; or $R^{10}$ is phenyl which may be optionally substituted with at least one substituent selected from the group consisting of $C_1$–$C_4$ alkyl, $C_1$–$C_4$ alkylthio groups, halogen atoms, hydroxyl groups, trifluoromethyl, and cyano; or $R^{10}$ may be with a formula (a) as shown below:

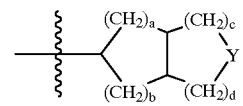

a wherein

Y is O, S or —CH$_2$—, a, b, c, and d is each independently an integer ranging from 0–2 and a+b+c+d$\leq$5;

$R^{11}$ is hydrogen or —OH; and $R^{15}$ is H, $C_1$–$C_{10}$ alkyl, $C_2$–$C_{10}$ alkenyl, $C_2$–$C_{10}$ alkynyl, cyano, —CH$_2$S(O)$_p$$C_1$–$C_{10}$ alkyl, —CH$_2$S(O)$_p$$C_2$–$C_{10}$ alkenyl, —CH$_2$S(O)$_p$$C_2$–$C_{10}$ alkynyl, wherein p is an integer ranging from 0 to 2, —CH$_2$O($C_1$–$C_{10}$ alkyl), —CH$_2$O($C_2$–$C_{10}$ alkenyl), —CH$_2$O($C_2$–$C_{10}$ alkynyl), —CH$_2$N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), —$(CH_2)_m(C_6$–$C_{10}$ aryl) or —$(CH_2)_m$(5–10 membered heteroaryl), wherein m is an integer ranging from 0 to 4, and wherein the alkyl, alkenyl, alkynyl, aryl and heteroaryl moieties of the foregoing are optionally substituted with 1 to 3 substituents independently selected from the group consisting of halo, cyano, nitro, trifluoromethyl, azido, —C(O)$C_1$–$C_{10}$ alkyl, —C(O)$C_2$–$C_{10}$ alkenyl, —C(O) $C_2$–$C_{10}$ alkynyl, —OC(O)$C_1$–$C_{10}$ alkyl, —OC(O) $C_2$–$C_{10}$ alkenyl, —OC(O)$C_2$–$C_{10}$ alkynyl, —N(hydrogen, $C_1$–$C_{10}$ alkyl, $C_2$–$C_{10}$ alkenyl or $C_2$–$C_{10}$ alkynyl)C(O)($C_1$–$C_{10}$ alkyl, $C_2$–$C_{10}$ alkenyl or $C_2$–$_{10}$ alkynyl), —C(O)N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), —N(hydrogen, $C_1$–$C_{10}$ alkyl, $C_2$–$C_{10}$ alkenyl or- $C_2$–$C_{10}$ alkynyl)(hydrogen, $C_1$–$C_{10}$ alkyl, $C_2$–$C_{10}$ alkenyl or $C_2$–$C_{10}$ alkynyl), $C_1$–$C_{10}$ alkoxy, $C_6$–$C_{10}$ aryl or 5–10 membered heterocyclic, hydroxy, $C_1$–$C_6$ alkyl, $C_1$–$C_6$ alkoxy, $C_6$–$C_{10}$ aryl and 5–10 membered heteroaryl, except that when $R^{15}$ is H, $R^{10}$ is not ethyl.

3. The compound of claim 2 wherein $R^1$ is

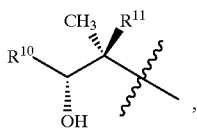

$R^2$ is $CH_3$, $R^6$ is $R^7$ is $R^8$ is H and $R^9$ is cladinosyl.

4. The compound of claim 1 wherein $R^1$ is

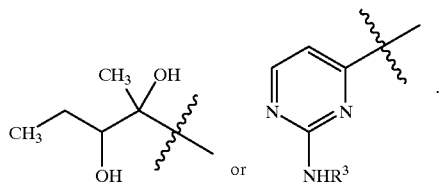

5. The compound of any of claims 1, 2 or 3 wherein $R^7$ and $R^8$ are hydrogen.

6. The compound of claim 1 wherein $R^9$ is

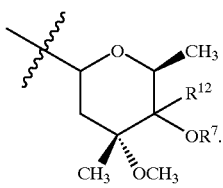

7. The compound of claim 2 wherein $R^9$ is

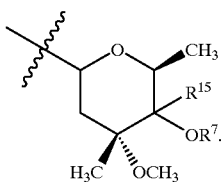

8. The compound of claim 1 or 3 wherein $R^{12}$ is

—$CH_2N$(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl).

9. The compound of claim 2 wherein $R^{15}$ is —$CH_2N$ (hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl).

10. The compound of any of claims 1, 2 or 3 wherein $R^7$ is H, acetyl, or benzyloxycarbonyl.

11. The compound of claim 2 having the formula 3

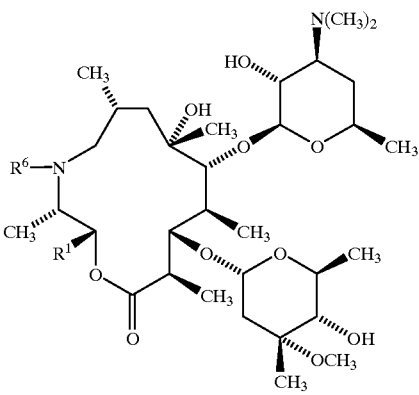

12. A compound having the formula 3

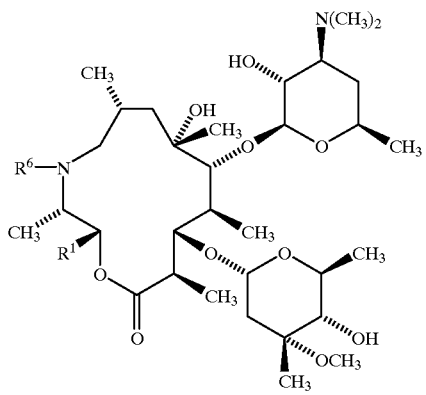

selected from the group consisting of:
the compound wherein $R^1$ is acetyl and $R^6$ is hydrogen;
the compound wherein $R^1$ is 3-N,N-dimethylamino-2-propenoyl and $R^6$ is hydrogen;
the compound wherein $R^1$ is 3-pyrazolyl and $R^6$ is hydrogen;
the compound wherein $R^1$ is acetyl and $R^6$ is methyl;
the compound wherein $R^1$ is 3-N,N-dimethylamino-2-propenoyl and $R^6$ is methyl;
the compound wherein $R^1$ is 3-pyrazolyl and $R^6$ is methyl;
the compound wherein $R^1$ is 1-N-methyl-3-pyrazolyl and $R^6$ is methyl;
the compound wherein $R^1$ is 1-N-benzyl-3-pyrazolyl and $R^6$ is methyl;
the compound wherein $R^1$ is 1-N-(3-hydroxybenzyl)-3-pyrazolyl and $R^6$ is methyl;
the compound wherein $R^1$ is 2-(4-fluorophenyl)-3-pyrimidinyl and $R^6$ is methyl;
the compound wherein $R^1$ is 2-(phenylamino)-3-pyrimidinyl and $R^6$ is methyl; and
the compound wherein $R^1$ is 1-N-methyl-5-pyrazolyl and $R^6$ is methyl.

13. A compound of the formula 14:

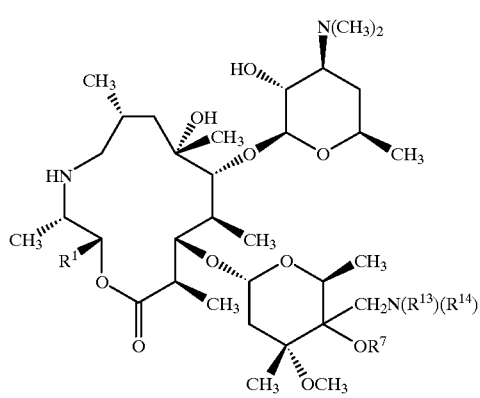

or a pharmaceutically acceptable salt thereof, wherein:

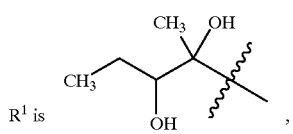

acetyl, 3-N,N-dimethylamino-2-propenoyl,

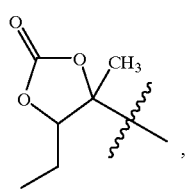

1-N-methyl-5-pyrazolyl, 3-pyrazolyl, 1-methyl-N-3-pyrazolyl, 1-N-benzyl-3-pyrazolyl, 1-N-(3-hydroxybenzyl)-3-pyrazolyl, 3-isoxazolyl,

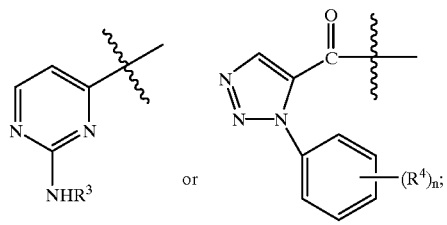

$R^7$ is independently hydrogen, $C_1$–$C_{20}$ alkyl, $C_2$–$C_{20}$ alkenyl, $C_2$–$C_{20}$ alkynyl, —C(O)$C_1$–$C_{20}$ alkyl, —C(O) $C_2$–$C_{20}$ alkenyl, —C(O)$C_2$–$C_{20}$ alkynyl, —C(O)N(H) $C_1$–$C_{10}$ alkyl, —C(O)N(H)$C_2$–$C_{20}$ alkenyl, —C(O)N (H)$C_2$–$C_{20}$ alkynyl, —SO$_2$(O)$C_1$–$C_{20}$ alkyl, —SO$_2$(O) $C_2$–$C_{20}$ alkenyl, —SO$_2$(O)$C_2$–$C_{20}$ alkynyl, or —PO$_4^{2-}$; and $R^{13}$ and $R^{14}$ are independently hydrogen or $C_1$–$C_6$ alkyl, $C_2$–$C_8$ alkenyl or $C_2$–$C_6$ alkynyl.

14. A compound of the formula 14:

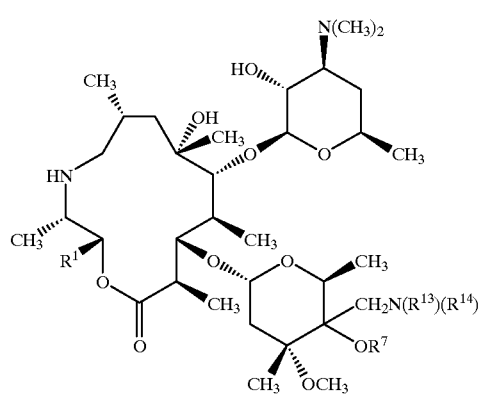

or a pharmaceutically acceptable salt thereof, wherein $R^1$ is

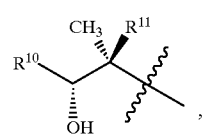

acetyl, 3-N,N-dimethylamino-2-propenoyl,

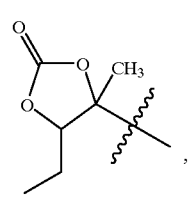

1-N-methyl-5-pyrazolyl, 3-pyrazolyl, 1-methyl-N-3-pyrazolyl, 1-N-benzyl-3-pyrazolyl, 1-N-(3-hydroxybenzyl)-3-pyrazolyl, 3-isoxazolyl,

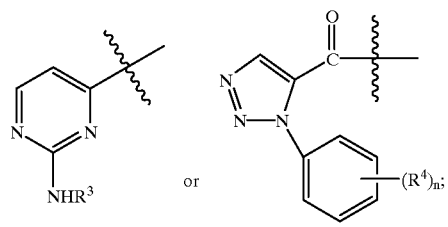

$R^7$ is independently hydrogen, $C_1$–$C_{20}$ alkyl, $C_2$–$C_{20}$ alkenyl, $C_2$–$C_{20}$ alkynyl, —C(O)$C_1$–$C_{20}$ alkyl, —C(O) $C_2$–$C_{20}$ alkenyl, —C(O)$C_2$–$C_{20}$ alkynyl, —C(O)N(H) $C_1$–$C_{10}$ alkyl, —C(O)N(H)$C_2$–$C_{20}$ alkenyl, —C(O)N (H)$C_2$–$C_{20}$ alkynyl, —SO$_2$(O)$C_1$–$C_{20}$ alkyl, —SO$_2$(O) $C_2$–$C_{20}$ alkenyl, —SO$_2$(O)$C_2$–$C_{20}$ alkynyl or —PO$_4^{2-}$; and $R^{13}$ and $R^{14}$ are independently hydrogen or $C_1$–$C_6$ alkyl, $C_2$–$C_6$ alkenyl or $C_2$–$C_6$ alkynyl.

15. The compound of claim 13 or 14 wherein $R^1$ is

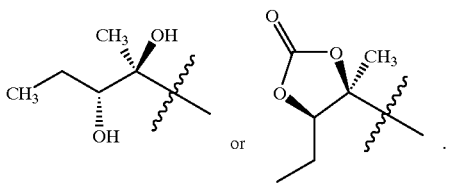

16. The compound of claim 1 or 2 in isolated or purified form.

17. A compound of the formula 2

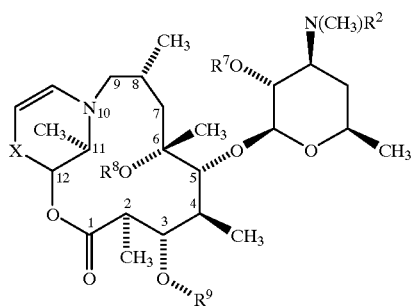

or a pharmaceutically acceptable salt thereof, wherein:

X is —C(O)— or —CH(OR$^7$)—;

$R^2$ is hydrogen or $C_1$–$C_4$ alkyl;

each $R^7$ is independently hydrogen, $C_1$–$C_{20}$ alkyl, $C_2$–$C_{20}$ alkenyl, $C_2$–$C_{20}$ alkynyl, —C(O)$C_1$–$C_{20}$ alkyl, —C(O)$C_1$–$C_{20}$ alkenyl, —C(O)$C_2$–$C_{20}$ alkynyl, —C(O)N(H)$C_1$–$C_{10}$ alkyl, —C(O)N(H)$C_2$–$C_{20}$ alkenyl, —C(O)N(H)$C_2$–$C_{20}$ alkynyl, —SO$_2$(O)$C_1$–$C_{20}$ alkyl, —SO$_2$(O)$C_2$–$C_{20}$ alkenyl, —SO$_2$(O)$C_2$–$C_{20}$ alkynyl or —PO$_4^{2-}$;

$R^8$ is hydrogen or methyl;

$R^9$ is

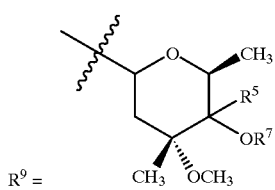

or 4"-oxocladinosyl; and $R^5$ is hydrogen, $C_1$–$C_{10}$ alkyl, $C_2$–$C_{10}$ alkenyl, $C_2$–$C_{10}$ alkynyl, cyano, —CH$_2$S(O)$_p$$C_1$–$C_{10}$ alkyl, —CH$_2$S(O)$_p$$C_2$–$C_{10}$ alkenyl, —CH$_2$S(O)$_p$$C_2$–$C_{10}$ alkynyl, wherein p is an integer ranging from 0 to 2, —CH$_2$O($C_1$–$C_{10}$ alkyl), —CH$_2$O($C_2$–$C_{10}$ alkenyl), —CH$_2$O($C_2$–$C_{10}$ alkynl), —CH$_2$N(hydrogen, $C_1$–$C_{10}$ alkyl, $C_2$–$C_{10}$ alkenyl or $C_1$–$C_{10}$ alkynyl)(hydrogen, $C_1$–$C_{10}$ alkyl, $C_2$–$C_{10}$ alkenyl or $C_2$–$C_{10}$ alkynyl), —(CH$_2$)$_m$($C_6$–$C_{10}$ aryl) or —(CH$_2$)$_m$(5–10 membered heteroaryl), wherein m is an integer ranging from 0 to 4, and wherein the alkyl, alkenyl, alkynyl, aryl and heteroaryl moieties of the foregoing are optionally substituted with 1 to 3 substituents independently selected from the group consisting of halo, cyano, nitro, trifluoromethyl, azido, —C(O)$C_1$–$C_{10}$ alkyl, —C(O)$C_2$–$C_{10}$ alkenyl, —C(O)$C_2$–$C_{10}$ alkynyl, —OC(O)$C_1$–$C_{10}$ alkyl, —OC(O)$C_2$–$C_{10}$ alkenyl, —OC(O)$C_2$–$C_{10}$ alkynyl, —N(hydrogen, $C_1$–$C_{10}$ alkyl, $C_2$–$C_{10}$ alkenyl or $C_2$–$C_{10}$ alkynyl)C(O)($C_1$–$C_{10}$ alkyl, $C_2$–$C_{10}$ alkenyl or $C_2$–$C_{10}$ alkynyl), —C(O)N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), —N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), $C_1$–$C_{10}$ alkoxy, $C_6$–$C_{10}$ aryl or 5–10 membered heterocyclic, hydroxy, $C_1$–$C_6$ alkyl, $C_1$–$C_6$ alkoxy, $C_6$–$C_{10}$ aryl and 5–10 membered heteroaryl.

18. The compound of claim 17 wherein $R^7$ and $R^8$ are hydrogen.

19. The compound of claim 17 wherein $R^9$ is

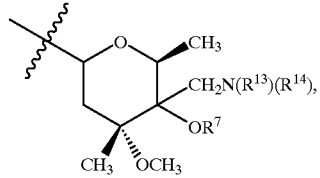

and $R^{13}$ and $R^{14}$ are independently hydrogen or $C_1$–$C_6$ alkyl, $C_2$–$C_6$ alkenyl or $C_2$–$C_6$ alkynyl.

20. The compound of claim 17 selected from the group consisting of:

the compound wherein X is —C(O)—; and the compound wherein X is —CH(OH)—.

21. The compound of claim 17 in isolated or purified form.

22. A pharmaceutical composition useful for the treatment of a bacterial infection or a protozoa infection in a mammal, fish, or bird which comprises a therapeutically effective amount of a compound of claim 1 or 2 and a pharmaceutically acceptable carrier.

23. A method of treating a bacterial infection or a protozoa infection in a mammal, fish, or bird which comprises administering to said mammal, fish or bird a therapeutically effective amount of a compound of claim 1 or 2.

24. A pharmaceutical composition useful for the treatment of a bacterial infection or a protozoa infection in a mammal, fish, or bird which comprises a therapeutically effective amount of a compound of claim 16 and a pharmaceutically acceptable carrier.

25. A method of treating a bacterial infection or a protozoa infection in a mammal, fish, or bird which comprises administering to said mammal, fish or bird a therapeutically effective amount of a compound of claim 16.

26. A method of preparing a compound of the formula

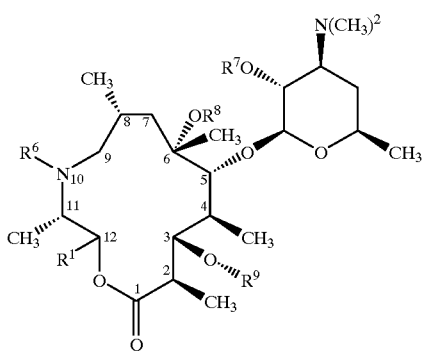

wherein

R¹ is trans with respect to the methyl group at position 11 of formula 1, and is

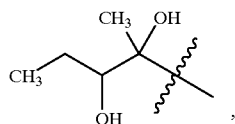

acetyl, 3-N,N-dimethylamino-2-propenoyl,

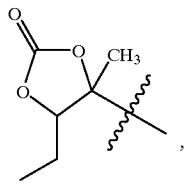

1-N-methyl-5-pyrazolyl, 3-pyrazolyl, 1-methyl-N-3-pyrazolyl, 1-N-benzyl-3-pyrazolyl, 1-N-(-hydroxybenzyl)-3-pyrazolyl, 3-isoxazolyl,

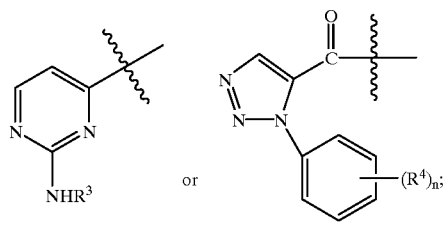

$R^2$ is hydrogen or $C_1$–$C_4$ alkyl;

$R^3$ is hydrogen, $C_1$–$C_{10}$ alkyl, $C_2$–$C_{10}$ alkenyl, $C_2$–$C_{10}$ alkynyl, —$(CH_2)_m(C_6$–$C_{10}$ aryl), or —$(CH_2)_m(C_6$–$C_{10}$ heterocyclic), each, other than hydrogen, being optionally substituted with 1 to 3 substituents independently selected from the group consisting of halogen, cyano, nitro, trifluoromethyl, azido, —$C(O)C_1$–$C_{10}$ alkyl, —$C(O)C_2$–$C_{10}$ alkenyl, —$C(O)C_2$–$C_{10}$ alkynyl, —OC(O)$C_1$–$C_{10}$ alkyl, —OC(O)$C_2$–$C_{10}$ alkenyl, —OC(O)$C_2$–$C_{10}$ alkynyl, —N(hydrogen, $C_1$–$C_{10}$ alkyl, $C_2$–$C_{10}$ alkenyl or $C_2$–$C_{10}$ alkynyl)C(O)($C_1$–$C_{10}$ alkyl, $C_2$–$C_{10}$ alkenyl or $C_2$–$C_{10}$ alkynyl), —C(O)N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), —N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), $C_1$–$C_{10}$ alkoxy, $C_6$–$C_{10}$ aryl, 5–10 membered heterocyclic, hydroxyl, methoxyl, $C_1$–$C_{10}$ alkyl, $C_2$–$C_{10}$ alkenyl, $C_2$–$C_{10}$ alkynyl, 2-pyridyl, 3-pyridyl, 4-pyridyl, 2-pyrimidyl, 4-pyrimidyl, 2-pyridylmethyl, 3-pyridylmethyl, 4-pyridylmethyl, 2-pyridylethyl, 3-pyridylethyl and 4-pyridylethyl;

m is an integer ranging from 0 to 4;

each $R^4$ is hydrogen, —$(CH_2)_m(C_6$–$C_{10}$ aryl) or —$(CH_2)_m(C_6$–$C_{10}$ heterocyclic), each, other than hydrogen, being optionally substituted with 1 to 3 substituents independently selected from the group consisting of the group consisting of halo, cyano, nitro, trifluoromethyl, azido, —$C(O)C_1$–$C_{10}$ alkyl, —$C(O)C_2$–$C_{10}$ alkenyl, —$C(O)C_2$–$C_{10}$ alkynyl, —OC(O)$C_1$–$C_{10}$ alkyl, —OC(O)$C_2$–$C_{10}$ alkenyl, —OC(O)$C_2$–$C_{10}$ alkynyl, —N(hydrogen, $C_1$–$C_{10}$ alkyl, $C_2$–$C_{10}$ alkenyl or $C_2$–$C_{10}$ alkynyl)C(O)($C_1$–$C_{10}$ alkyl, $C_2$–$C_{10}$ alkenyl or $C_2$–$C_{10}$ alkynyl), —C(O)N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), —N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), $C_1$–$C_{10}$ alkoxy, $C_6$–$C_{10}$ aryl and 5–10 membered heterocyclic;

n is an integer from 0 to 5;

$R^6$, $R^7$ and $R^8$ are hydrogen;

$R^9$ is

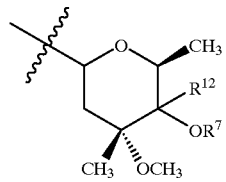

or 4"-oxocladinosyl; and $R^{12}$ is H, $C_1$–$C_{10}$ alkyl, $C_2$–$C_{10}$ alkenyl, $C_2$–$C_{10}$ alkynyl, cyano, —$CH_2S(O)_pC_1$–$C_{10}$ alkyl, —$CH_2S(O)_pC_2$–$C_{10}$ alkenyl, —$CH_2S(O)_pC_2$–$C_{10}$ alkynyl, wherein p is an integer ranging from 0 to 2, —$CH_2O(C_1$–$C_{10}$ alkyl), —$CH_2O(C_2$–$C_{10}$ alkenyl), —$CH_2O(C_2$–$C_{10}$ alkynyl), —$CH_2N$(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), —$(CH_2)_m(C_6$–$C_{10}$ aryl) or —$(CH_2)_m$(5–10 membered heteroaryl), wherein m is an integer ranging from 0 to 4, and wherein the alkyl, alkenyl, alkynyl, aryl and heteroaryl moieties of the foregoing are optionally substituted with 1 to 3 substituents independently selected from the group consisting of halo, cyano, nitro, trifluoromethyl, azido, —$C(O)C_1$–$C_{10}$ alkyl, —$C(O)C_2$–$C_{10}$ alkenyl, —$C(O)C_2$–$C_{10}$ alkynyl, —OC(O)$C_1$–$C_{10}$ alkyl, —OC(O)$C_2$–$C_{10}$ alkenyl, —OC(O)$C_2$–$C_{10}$ alkynyl, —N(hydrogen, $C_1$–$C_{10}$ alkyl, $C_2$–$C_{10}$ alkenyl or $C_2$–$C_{10}$ alkynyl)C(O)($C_1$–$C_{10}$ alkyl, $C_2$–$C_{10}$ alkenyl or $C_2$–$C_{10}$ alkynyl), —C(O)N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), —N(hydrogen, $C_1$–$C_{10}$ alkyl, $C_2$–$C_{10}$ alkenyl or

49

$C_2$–$C_{10}$ alkynyl)(hydrogen, $C_1$–$C_{10}$ alkyl, $C_2$–$C_{10}$ alkenyl or $C_2$–$C_{10}$ alkynyl), $C_1$–$C_{10}$ alkoxy, $C_6$–$C_{10}$ aryl or 5–10 membered heterocyclic, hydroxy, $C_1$–$C_6$ alkyl, $C_1$–$C_6$ alkoxy, $C_6$–$C_{10}$ aryl and 5–10 membered heteroaryl, which comprises the step of contacting a compound of the formula 5

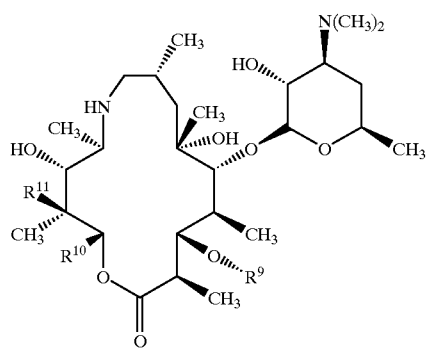

5 wherein $R^9$, is as defined in the compound of formula 1;

$R^{10}$ is an alpha-branched $C_2$–$C_8$ alkyl, alkenyl, alkynyl, alkoxyalkyl or alkylthioalkyl group, any of which may optionally be substituted by one or more hydroxyl groups; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methyl or one or more hydroxyl, one or more $C_1$–$C_4$ alkyl groups or halo atoms; or a 3 to 6 membered oxygen or sulphur containing heterocyclic ring which may be saturated, or fully or partially unsaturated and which may optionally be substituted by one or more $C_1$–$C_4$ alkyl groups or halo atoms; or $R^{10}$ is phenyl which may be optionally substituted with at least one substituent selected from the group consisting of $C_1$–$C_4$ alkyl, $C_1$–$C_4$ alkylthio groups, halogen atoms, hydroxyl groups, trifluoromethyl, and cyano; or $R^{10}$ may be with a formula (a) as shown below:

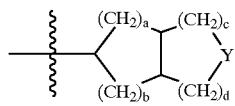

a wherein

Y is O, S or —$CH_2$—, a, b, c, and d is each independently an integer ranging from 0–2 and a+b+c+d≦5; and $R^{11}$ is hydrogen or —OH, with an acid or a base to result in the formation of a compound of formula 1.

50

27. A method of preparing a compound of the formula 15

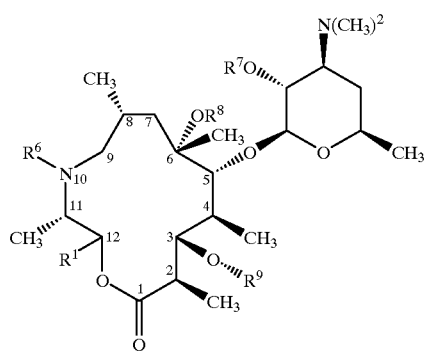

15 or a pharmaceutically acceptable salt thereof, wherein:

$R^1$ is 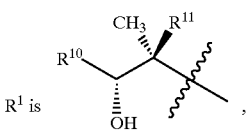, acetyl, 3-N,N-dimethylamino-2-propenoyl,

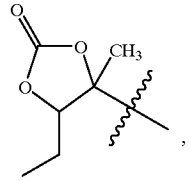,

1-N-methyl-5-pyrazolyl, 3-pyrazolyl, 1-methyl-N-3-pyrazolyl, 1-N-benzyl-3-pyrazolyl, 1-N-(3-hydroxybenzyl)-3-pyrazolyl, 3-isoxazolyl,

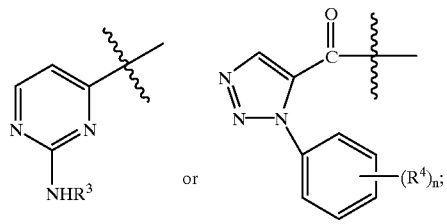;

$R^2$ is hydrogen or $C_1$–$C_4$ alkyl;

$R^3$ is hydrogen, $C_1$–$C_{10}$ alkyl, $C_2$–$C_{10}$ alkenyl, $C_2$–$C_{10}$ alkynyl, —$(CH_2)_m(C_6$–$C_{10}$ aryl), or —$(CH_2)_m(C_6$–$C_{10}$ heterocyclic), each, other than hydrogen, being optionally substituted with 1 to 3 substituents independently selected from the group consisting of halogen, cyano, nitro, trifluoromethyl, azido, —C(O)$C_1$–$C_{10}$ alkyl, —C(O)$C_2$–$C_{10}$ alkenyl, —C(O)$C_2$–$C_{10}$ alkynyl, —OC(O)$C_1$–$C_{10}$ alkyl, —OC(O)$C_2$–$C_{10}$ alkenyl, —OC(O)$C_2$–$C_{10}$ alkynyl, —N(hydrogen, $C_1$–$C_{10}$ alkyl, $C_2$–$C_{10}$ alkenyl or $C_2$–$C_{10}$ alkynyl)C(O)($C_1$–$C_{10}$ alkyl, $C_2$–$C_{10}$ alkenyl or $C_2$–$C_{10}$ alkynyl), —C(O)N(hydrogen, $C_1$–$C_{10}$ alkyl, $C_2$–$C_{10}$ alkenyl or $C_2$–$C_{10}$ alkynyl)

(hydrogen, $C_1$–$C_{10}$ alkyl, $C_2$–$C_{10}$ alkenyl or $C_2$–$C_{10}$ alkynyl), —N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), $C_1$–$C_{10}$ alkoxy, $C_6$–$C_{10}$ aryl, 5–10 membered heterocyclic, hydroxyl, methoxyl, $C_1$–$C_{10}$ alkyl, $C_2$–$C_{10}$ alkenyl, $C_2$–$C_{10}$ alkynyl, 2-pyridyl, 3-pyridyl, 4-pyridyl, 2-pyrimidyl, 4-pyrimidyl, 2-pyridylmethyl, 3-pyridylmethyl, 4-pyridylmethyl, 2-pyridylethyl, 3-pyridylethyl and 4-pyridylethyl;

m is an integer ranging from 0 to 4;

each $R^4$ is hydrogen, —$(CH_2)_m(C_6$–$C_{10}$ aryl) or —$(CH_2)_m(C_6$–$C_{10}$ heterocyclic), each, other than hydrogen, being optionally substituted with 1 to 3 substituents independently selected from the group consisting of halo, cyano, nitro, trifluoromethyl, azido, —$C(O)C_1$–$C_{10}$ alkyl, —$C(O)C_2$–$C_{10}$ alkenyl, —$C(O)C_2$–$C_{10}$ alkynyl, —$OC(O)C_1$–$C_{10}$ alkyl, —$OC(O)C_2$–$C_{10}$ alkenyl, —$OC(O)C_2$–$C_{10}$ alkynyl, —N(hydrogen, $C_1$–$C_{10}$ alkyl, $C_2$–$C_{10}$ alkenyl or $C_2$–$C_{10}$ alkynyl)C(O)($C_1$–$C_{10}$ alkyl, $C_2$–Calkenyl or $C_2$–$C_{10}$ alkynyl), —C(O)N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), —N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), $C_1$–$C_{10}$ alkoxy, $C_6$–$C_{10}$ aryl and 5–10 membered heterocyclic;

n is an integer from 0 to 5;

$R^6$ is hydrogen or methyl;

each $R^7$ is independently hydrogen, $C_1$–$C_{20}$ alkyl, $C_2$–$C_{20}$ alkenyl, $C_2$–$C_{20}$ alkynyl, —$C(O)C_1$–$C_{20}$ alkyl, —$C(O)C_2$–$C_{20}$ alkenyl, —$C(O)C_2$–$C_{20}$ alkynyl, —C(O)N(H)$C_1$–$C_{10}$ alkyl, —C(O)N(H)$C_2$–$C_{20}$ alkenyl, —C(O)N(H)$C_2$–$C_{20}$ alkynyl, —$SO_2(O)C_1$–$C_{20}$ alkyl, —$SO_2(O)C_2$–$C_{20}$ alkenyl, —$SO_2(O)C_2$–$C_{20}$ alkynyl or —$PO_4^{2-}$;

$R^8$ is hydrogen or methyl;

$R^9$ is

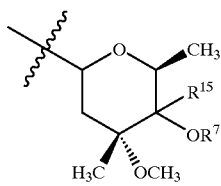

or 4''-oxocladinosyl;

$R^{10}$ is an alpha-branched $C_2$–$C_8$ alkyl, alkenyl, alkynyl, alkoxyalkyl or alkylthioalkyl group, any of which may optionally be substituted by one or more hydroxyl groups; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methyl or one or more hydroxyl, one or more $C_1$–$C_4$ alkyl groups or halo atoms; or a 3 to 6 membered oxygen or sulphur containing heterocyclic ring which may be saturated, or fully or partially unsaturated and which may optionally be substituted by one or more $C_1$–$C_4$ alkyl groups or halo atoms; or $R^{10}$ is phenyl which may be optionally substituted with at least one substituent selected from the group consisting of $C_1$–$C_4$ alkyl, $C_1$–$C_4$ alkylthio groups, halogen atoms, hydroxyl groups, trifluoromethyl, and cyano; or $R^{10}$ may be with a formula (a) as shown below:

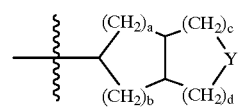

wherein

Y is O, S or —$CH_2$—, a, b, c, and d is each independently an integer ranging from 0–2 and a+b+c+d≦5;

$R^{11}$ is hydrogen or —OH; and $R^{15}$ is H, $C_1$–$C_{10}$ alkyl, $C_2$–$C_{10}$ alkenyl, $C_2$–$C_{10}$ alkynyl, cyano, —$CH_2S(O)_pC_1$–$C_{10}$ alkyl, —$CH_2S(O)_pC_2$–$C_{10}$ alkenyl, —$CH_2S(O)_pC_2$–$C_{10}$ alkynyl, wherein p is an integer ranging from 0 to 2, —$CH_2O(C_1$–$C_{10}$ alkyl), —$CH_2O(C_2$–$C_{10}$ alkenyl), —$CH_2O(C_2$–Calkynyl), —$CH_2N$(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), —$(CH_2)_m(C_6$–$C_{10}$ aryl) or —$(CH_2)_m$(5–10 membered heteroaryl), wherein m is an integer ranging from 0 to 4, and wherein the alkyl, alkenyl, alkynyl, aryl and heteroaryl moieties of the foregoing are optionally substituted with 1 to 3 substituents independently selected from the group consisting of halo, cyano, nitro, trifluoromethyl, azido, —$C(O)C_1$–$C_{10}$ alkyl, —$C(O)C_2$–$C_{10}$ alkenyl, —$C(O)C_2$–$C_{10}$ alkynyl, —$OC(O)C_1$–$C_{10}$ alkyl, —$OC(O)C_2$–$C_{10}$ alkenyl, —$OC(O)C_2$–$C_{10}$ alkynyl, —N(hydrogen, $C_1$–$C_{10}$ alkyl, $C_2$–$C_{10}$ alkenyl or $C_2$–$C_{10}$ alkynyl)C(O)($C_1$–$C_{10}$ alkyl, $C_2$–$C_{10}$ alkenyl or $C_2$–$C_{10}$ alkynyl), —C(O)N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), —N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), $C_1$–$C_{10}$ alkoxy, $C_6$–$C_{10}$ aryl or 5–10 membered heterocyclic, hydroxy, $C_1$–$C_6$ alkyl, $C_1$–$C_6$ alkoxy, $C_6$–$C_{10}$ aryl and 5–10 membered heteroaryl, which comprises the step of contacting a compound of the formula 5

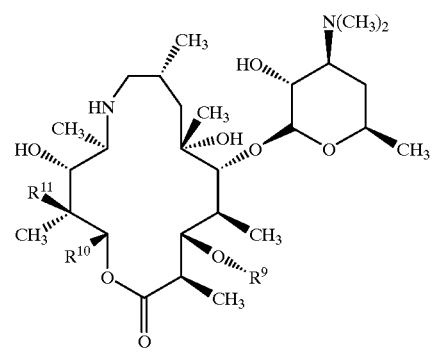

wherein $R^9$, $R^{10}$ and $R^{11}$ are defined above, with an acid or a base, to result in the formation of the compound of formula 15.

28. A method of preparing a compound of the formula 1

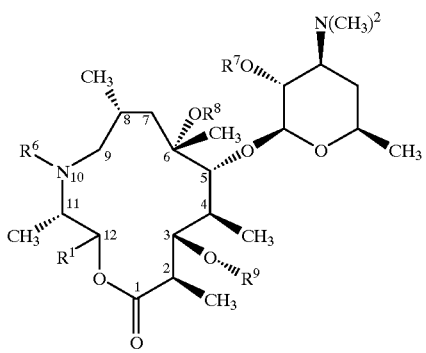

wherein

R¹ is trans with respect to the methyl group at position 11 of formula 1, and is

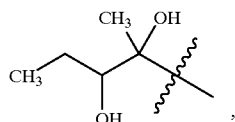

acetyl, 3-N,N-dimethylamino-2-propenoyl,

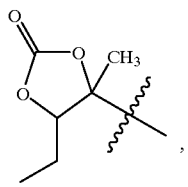

1-N-methyl-5-pyrazolyl, 3-pyrazolyl, 1-methyl-N-3-pyrazolyl, 1-N-benzyl-3-pyrazolyl, 1-N-(3-hydroxybenzyl)-3-pyrazolyl, 3-isoxazolyl,

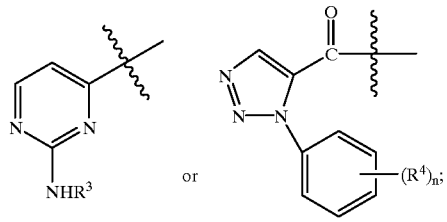

$R^2$ is hydrogen or $C_1$–$C_4$ alkyl;

$R^3$ is hydrogen, $C_1$–$C_{10}$ alkyl, $C_2$–$C_{10}$ alkenyl, $C_2$–$C_{10}$ alkynyl, —$(CH_2)_m(C_6$–$C_{10}$ aryl), or —$(CH_2)_m(C_6$–$C_{10}$ heterocyclic), each, other than hydrogen, being optionally substituted with 1 to 3 substituents independently selected from the group consisting of halogen, cyano, nitro, trifluoromethyl, azido, —$C(O)C_1$–$C_{10}$ alkyl, —$C(O)C_2$–$C_{10}$ alkenyl, —$C(O)C_2$–$C_{10}$ alkynyl, —$OC(O)C_1$–$C_{10}$ alkyl, —$OC(O)C_2$–$C_{10}$ alkenyl, —$OC(O)C_2$–$C_{10}$ alkynyl, —N(hydrogen, $C_1$–$C_{10}$ alkyl, $C_2$–$C_{10}$ alkenyl or $C_2$–$C_{10}$ alkynyl)C(O)($C_1$–$C_{10}$ alkyl, $C_2$–$C_{10}$ alkenyl or $C_2$–$C_{10}$ alkynyl), —C(O)N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), —N(hydrogen, $C_1$–$C_{10}$ alkyl, $C_2$–$C_{10}$ alkynyl)(hydrogen, $C_1$–$C_{10}$ alkyl, $C_2$–$C_{10}$ alkenyl or $C_2$–$C_{10}$ alkynyl), —N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), $C_1$–$C_{10}$ alkoxy, $C_6$–$C_{10}$ aryl, 5–10 membered heterocyclic, hydroxyl, methoxyl, $C_1$–$C_{10}$ alkyl, $C_2$–$C_{10}$ alkenyl, $C_2$–$C_{10}$ alkynyl, 2-pyridyl, 3-pyridyl, 4-pyridyl, 2-pyrimidyl, 4-pyrimidyl, 2-pyridylmethyl, 3-pyridylmethyl, 4-pyridylmethyl, 2-pyridylethyl, 3-pyridylethyl and 4-pyridylethyl;

m is an integer ranging from 0 to 4;

each $R^4$ is hydrogen, —$(CH_2)_m(C_6$–$C_{10}$ aryl) or —$(CH_2)_m(C_6$–Cheterocyclic), each, other than hydrogen, being optionally substituted with 1 to 3 substituents independently selected from the group consisting of halo, cyano, nitro, trifluoromethyl, azido, —$C(O)C_1$–$C_{10}$ alkyl, —$C(O)C_2$–$C_{10}$ alkenyl, —$C(O)C_2$–$C_{10}$ alkynyl, —$OC(O)C_2$–$C_{10}$ alkyl, —$OC(O)C_2$–$C_{10}$ alkenyl, —$OC(O)C_2$–$C_{10}$ alkynyl, —N(hydrogen, $C_1$–$C_{10}$ alkyl, $C_2$–$C_{10}$ alkenyl or $C_2$–$C_{10}$ alkynyl)C(O)($C_1$–$C_{10}$ alkyl, $C_2$–$C_{10}$ alkenyl or $C_2$–$C_{10}$ alkynyl), —C(O)N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), —N(hydrogen, $C_1$–$C_{10}$ alkyl, $C_2$–$C_{10}$ alkynyl)(hydrogen, $C_1$–$C_{10}$ alkyl, $C_2$–$C_{10}$ alkenyl or $C_2$–$C_{10}$ alkynyl), —N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), $C_1$–$C_{10}$ alkoxy, $C_6$–$C_{10}$aryl and 5–10 membered heterocyclic;

n is an integer from 0 to 5;

$R^6$, $R^7$ and $R^8$ are hydrogen;

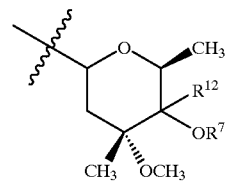

$R^9$ is or 4"-oxocladinosyl; and $R^{12}$ is H, $C_1$–$C_{10}$ alkyl, $C_2$–$C_{10}$ alkenyl, $C_2$–$C_{10}$ alkynyl, cyano, —$CH_2S(O)_pC_1$–$C_{10}$ alkyl, —$CH_2S(O)_pC_2$–$C_{10}$ alkenyl, —$CH_2S(O)_pC_2$–$C_{10}$ alkynyl, wherein p is an integer ranging from 0 to 2, —$CH_2O(C_1$–$C_{10}$ alkyl), —$CH_2O(C_2$–$C_{10}$ alkenyl), —$CH_2O(C_2$–$C_{10}$ alkynyl), —$CH_2N$(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), —$(CH_2)_m(C_6$–$C_{10}$ aryl) or —$(CH_2)_m$(5–10 membered heteroaryl), wherein m is an integer ranging from 0 to 4, and wherein the alkyl, alkenyl, alkynyl, aryl and heteroaryl moieties of the foregoing are optionally substituted with 1 to 3 substituents independently selected from the group consisting of halo, cyano, nitro, trifluoromethyl, azido, —$C(O)C_1$–$C_{10}$alkyl, —$C(O)C_2$–$C_{10}$ alkenyl, —$C(O)C_2$–$C_{10}$ alkynyl, —$OC(O)C_1$–$C_{10}$ alkyl, —$OC(O)C_2$–$C_{10}$ alkenyl, —$OC(O)C_2$–$C_{10}$ alkynyl, —N(hydrogen, $C_1$–$C_{10}$ alkyl, $C_2$–$C_{10}$ alkenyl or $C_2$–$C_{10}$ alkynyl)C(O)($C_1$–$C_{10}$ alkyl, $C_2$–$C_{10}$ alkenyl or $C_2$–$C_{10}$ alkynyl), —C(O)N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), —N(hydrogen, $C_1$–$C_{10}$ alkyl, $C_2$–$C_{10}$ alkenyl or C$_2$–C$_{10}$ alkynyl)(hydrogen, C$_1$–C$_{10}$ alkyl, C$_2$–C$_{10}$ alkenyl or C$_2$–C$_{10}$ alkynyl), C$_1$–C$_{10}$ alkoxy, C$_6$–C$_{10}$ aryl or 5–10 membered heterocyclic, hydroxy, C$_1$–C$_6$ alkyl, C$_1$–C$_6$ alkoxy, C$_6$–C$_{10}$ aryl and 5–10 membered heteroaryl, which comprises the step of heating a compound of the formula 5

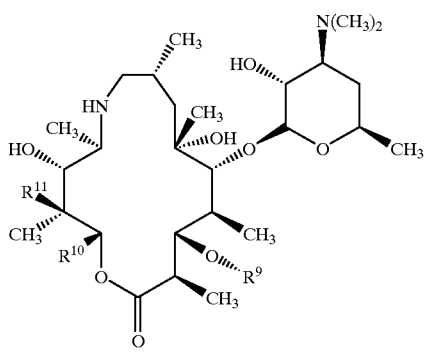

wherein

R$^9$, is as defined in the compound of formula 1;

R$^{10}$ is an alpha-branched C$_2$–C$_8$ alkyl, alkenyl, alkynyl, alkoxyalkyl or alkylthioalkyl group, any of which may optionally be substituted by one or more hydroxyl groups; a C$_5$–C$_8$ cycloalkylalkyl group wherein the alkyl group is an alpha-branched C$_2$–C$_5$ alkyl group; a C$_3$–C$_8$ cycloalkyl or C$_5$–C$_8$ cycloalkenyl group, either of which may optionally be substituted by methyl or one or more hydroxyl, one or more C$_1$–C$_4$ alkyl groups or halo atoms; or a 3 to 6 membered oxygen or sulphur containing heterocyclic ring which may be saturated, or fully or partially unsaturated and which may optionally be substituted by one or more C$_1$–C$_4$ alkyl groups or halo atoms; or R$^{10}$ is phenyl which may be optionally substituted with at least one substituent selected from the group consisting of C$_1$–C$_4$ alkyl, C$_1$–C$_4$ alkylthio groups, halogen atoms, hydroxyl groups, trifluoromethyl, and cyano; or R$^{10}$ may be with a formula (a) as shown below:

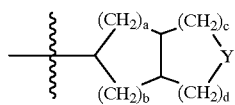

a wherein

Y is O, S or —CH$_2$—, a, b, c, and d is each independently an integer ranging from 0–2 and a+b+c+d≦5; and R$^{11}$ is hydrogen or —OH, in the presence of a solvent system, to result in the formation of the compound of formula 1.

29. A method of preparing a compound of the formula 15

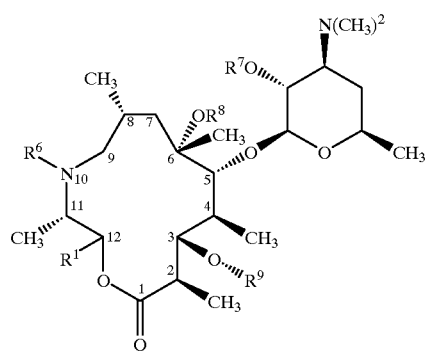

15 or a pharmaceutically acceptable salt thereof, wherein:

R$^1$ is 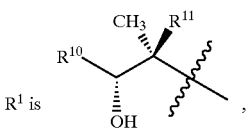, acetyl, 3-N,N-dimethylamino-2-propenoyl,

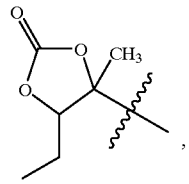,

1-N-methyl-5-pyrazolyl, 3-pyrazolyl, 1-methyl-N-3-pyrazolyl, 1-N-benzyl-3-pyrazolyl, 1-N-(3-hydroxybenzyl) 3-pyrazolyl, 3-isoxazolyl,

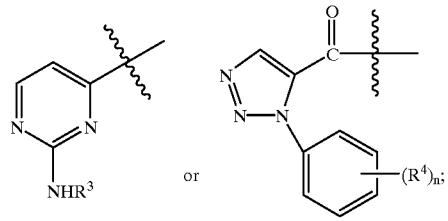

R$^2$ is hydrogen or C$_1$–C$_4$ alkyl;

R$^3$ is hydrogen, C$_1$–C$_{10}$ alkyl, C$_2$–C$_{10}$ alkenyl, C$_2$–C$_{10}$ alkynyl, —(CH$_2$)$_m$(C$_6$–C$_{10}$ aryl), or —(CH$_2$)$_m$(C$_6$–C$_{10}$ heterocyclic), each, other than hydrogen, being optionally substituted with 1 to 3 substituents independently selected from the group consisting of halogen, cyano, nitro, trifluoromethyl, azido, —C(O)C$_1$–C$_{10}$ alkyl, —C(O)C$_2$–C$_{10}$ alkenyl, —C(O)C$_2$–C$_{10}$ alkynyl, —OC(O)C$_1$–C$_{10}$ alkyl, —OC(O)C$_2$–C$_{10}$ alkenyl, —OC(O)C$_2$–C$_{10}$ alkynyl, —N(hydrogen, C$_1$–C$_{10}$ alkyl, C$_2$–C$_{10}$ alkenyl or C$_2$–C$_{10}$ alkynyl)C(O)(C$_1$–C$_{10}$ alkyl, C$_2$–C$_{10}$alkenyl or C$_2$–C$_{10}$ alkynyl), —C(O)N (hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), —N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), $C_1$–$C_{10}$ alkoxy, $C_6$–$C_{10}$ aryl, 5–10 membered heterocyclic, hydroxyl, methoxyl, $C_1$–$C_{10}$ alkyl, $C_2$–$C_{10}$ alkenyl, $C_2$–$C_{10}$ alkynyl, 2-pyridyl, 3-pyridyl, 4-pyridyl, 2-pyrimidyl, 4-pyrimidyl, 2-pyridylmethyl, 3-pyridylmethyl, 4-pyridylmethyl, 2-pyridylethyl, 3-pyridylethyl and 4-pyridylethyl;

m is an integer ranging from 0 to 4;

each $R^4$ is hydrogen, —$(CH_2)_m(C_6$–$C_{10}$ aryl) or —$(CH_2)_m(C_6$–$C_{10}$ heterocyclic), each, other than hydrogen, being optionally substituted with 1 to 3 substituents independently selected from the group consisting of halo, cyano, nitro, trifluoromethyl, azido, —$C(O)C_1$–$C_{10}$ alkyl, —$C(O)C_2$–$C_{10}$ alkenyl, —$C(O)C_2$–$C_{10}$ alkynyl, —$OC(O)C_1$–$C_{10}$ alkyl, —$OC(O)C_2$–$C_{10}$ alkenyl, —$OC(O)C_2$–$C_{10}$ alkynyl, —N(hydrogen, $C_1$–$C_{10}$ alkyl, $C_2$–$C_{10}$ alkenyl or $C_2$–$C_{10}$ alkynyl)$C(O)(C_1$–$C_{10}$ alkyl, $C_2$–$C_{10}$ alkenyl or $C_2$–$C_{10}$ alkynyl), —$C(O)$N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), —N(hydrogen, $C_1$–$C_{10}$ alkyl, $C_2$–$C_{10}$ alkenyl or $C_2Cl_{10}$ alkynyl)(hydrogen, $C_1$–$C_{10}$ alkyl, $C_2$–$C_{10}$ alkenyl or $C_2$–$C_{10}$ alkynyl), $C_1$–$C_{10}$ alkoxy, $C_6$–$C_{10}$ aryl and 5–10 membered heterocyclic;

n is an integer from 0 to 5;

$R^6$ is hydrogen or methyl;

each $R^7$ is independently hydrogen, $C_1$–$C_{20}$ alkyl, $C_2$–$C_{20}$ alkenyl, $C_2$–$C_{20}$ alkynyl, —$C(O)C_1$–$C_{20}$ alkyl, —$C(O)C_2$–$C_{20}$ alkenyl, —$C(O)C_2$–$C_{20}$ alkynyl, —$C(O)N(H)C_1$–$C_{10}$ alkyl, —$C(O)N(H)C_2$–$C_{20}$ alkenyl, —$C(O)N(H)C_2$–$C_{20}$ alkynyl, —$SO_2(O)C_1$–$C_{20}$ alkyl, —$SO_2(O)C_2$–$C_{20}$ alkenyl, —$SO_2(O)C_2$–$C_{20}$ alkynyl or —$PO_4^{2-}$;

$R^8$ is hydrogen or methyl;

$R^9$ is

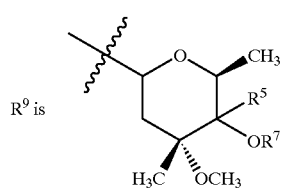

or 4″-oxocladinosyl;

$R^{10}$ is an alpha-branched $C_2$–$C_8$ alkyl, alkenyl, alkynyl, alkoxyalkyl or alkylthioalkyl group, any of which may optionally be substituted by one or more hydroxyl groups; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methyl or one or more hydroxyl, one or more $C_1$–$C_4$ alkyl groups or halo atoms; or a 3 to 6 membered oxygen or sulphur containing heterocyclic ring which may be saturated, or fully or partially unsaturated and which may optionally be substituted by one or more $C_1$–$C_4$ alkyl groups or halo atoms; or $R^{10}$ is phenyl which may be optionally substituted with at least one substituent selected from the group consisting of $C_1$–$C_4$ alkyl, $C_1$–$C_4$ alkylthio groups, halogen atoms, hydroxyl groups, trifluoromethyl, and cyano; or $R^{10}$ may be with a formula (a) as shown below:

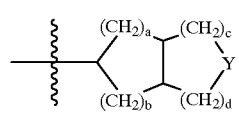

wherein

Y is O, S or —$CH_2$—, a, b, c, and d is each independently an integer ranging from 0–2 and $a+b+c+d \leq 5$;

$R^{11}$ is hydrogen or —OH; and $R^{15}$ is H, $C_1$–$C_{10}$ alkyl, $C_2$–$C_{10}$ alkenyl, $C_2$–$C_{10}$ alkynyl, cyano, —$CH_2S(O)_pC_1$–$C_{10}$ alkyl, —$CH_2S(O)_p(C_2$–$C_{10}$ alkenyl), —$CH_2S(O)_p(C_2$–$C_{20}$ alkynyl), wherein p is an integer ranging from 0 to 2 $C_1$–$C_{10}$ alkyl, $C_2O(C_2$–$C_{10}$ alkenyl); —$CH_2O(C_2$–$C_{10}$ alkynyl), —$CH_2$N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), —$(CH_2)_m(C_6$–$C_{10}$ aryl) or —$(CH_2)_m$(5–10 membered heteroaryl), wherein m is an integer ranging from 0 to 4, and wherein the alkyl, alkenyl, alkynyl, aryl and heteroaryl moieties of the foregoing are optionally substituted with 1 to 3 substituents independently selected from the group consisting of halo, cyano, nitro, trifluoromethyl, azido, —$C(O)C_1$–$C_{10}$ alkyl, —$C(O)C_2$–$C_{10}$ alkenyl, —$C(O)C_2$–$C_{10}$ alkynyl, —$OC(O)C_1$–$C_{10}$ alkyl, —$OC(O)C_2$–$C_{10}$ alkenyl, —$OC(O)C_2$–$C_{10}$ alkynyl, —N(hydrogen, $C_1$–$C_{10}$ alkyl, $C_2$–$C_{10}$ alkenyl or $C_2$–$C_{10}$ alkynyl)$C(O)(C_1$–$C_{10}$ alkyl, $C_2$–$C_{10}$ alkenyl or $C_2$–$C_{10}$ alkynyl), —$C(O)$N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), —N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), $C_1$–$C_{10}$ alkoxy, $C_6$–$C_{10}$ aryl or 5–10 membered heterocyclic, hydroxy, $C_1$–$C_6$ alkyl, $C_1$–$C_6$ alkoxy, $C_6$–$C_{10}$ aryl and 5–10 membered heteroaryl, which comprises the step of heating a compound of the formula 5

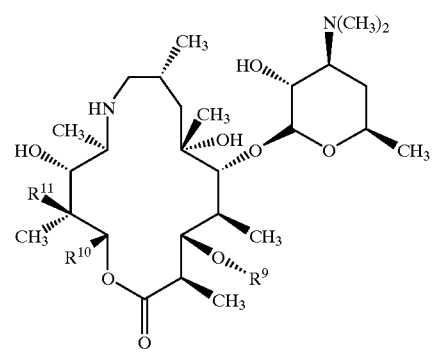

wherein $R^9$, $R^{10}$ and $R^{11}$ are as defined above;

in the presence of a solvent system, to result in the formation of the compound of formula 15.

30. A method of preparing a compound of the formula 15

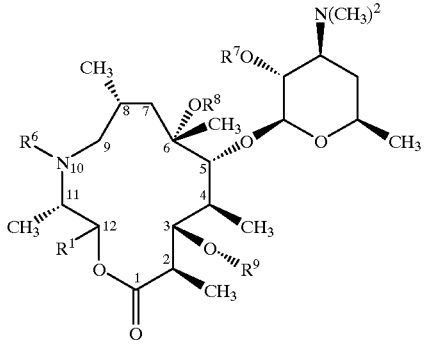

or a pharmaceutically acceptable salt thereof, wherein:

$R^1$ is 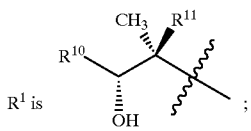 ;

$R^2$ is hydrogen or $C_1$–$C_4$ alkyl;

$R^3$ is hydrogen, $C_1$–$C_{10}$ alkyl, $C_2$–$C_{10}$ alkenyl, $C_2$–$C_{10}$ alkynyl, —(CH$_2$)$_m$(C$_6$–C$_{10}$ aryl), or —(CH$_2$)$_m$(C$_6$–C$_{10}$ heterocyclic), each, other than hydrogen, being optionally substituted with 1 to 3 substituents independently selected from the group consisting of halogen, cyano, nitro, trifluoromethyl, azido, —C(O)C$_1$–C$_{10}$ alkyl, —C(O)C$_2$–C$_{10}$ alkenyl, —C(O)C$_2$–C$_{10}$ alkynyl, —OC(O)C$_1$–C$_{10}$ alkyl, —OC(O)C$_2$–C$_{10}$ alkenyl, —OC(O)C$_2$–C$_{10}$ alkynyl, —N(hydrogen, $C_1$–$C_{10}$ alkyl, $C_2$–$C_{10}$ alkenyl or $C_2$–$C_{10}$ alkynyl)C(O)(C$_1$–C$_{10}$ alkyl, $C_2$–$C_{10}$ alkenyl or $C_2$–$C_{10}$ alkynyl), —C(O)N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), —N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), $C_1$–$C_{10}$ alkoxy, $C_6$–$C_{10}$ aryl, 5–10 membered heterocyclic, hydroxyl, methoxyl, $C_1$–$C_{10}$ alkyl, $C_2$–$C_{10}$ alkenyl, $C_2$–$C_{10}$ alkynyl, 2-pyridyl, 3-pyridyl, 4-pyridyl, 2-pyrimidyl, 4-pyrimidyl, 2-pyridylmethyl, 3-pyridylmethyl, 4-pyridylmethyl, 2-pyridylethyl, 3-pyridylethyl and 4-pyridylethyl;

m is an integer ranging from 0 to 4;

each $R^4$ is hydrogen, —(CH$_2$)$_m$(C$_6$–C$_{10}$ aryl) or —(CH$_2$)$_m$(C$_6$–C$_{10}$ heterocyclic), each, other than hydrogen, being optionally substituted with 1 to 3 substituents independently selected from the group consisting of halo, cyano, nitro, trifluoromethyl, azido, —C(O)C$_1$–C$_{10}$ alkyl, —C(O)C$_2$–C$_{10}$ alkenyl, —C(O)C$_2$–C$_{10}$ alkynyl, —OC(O)C$_1$–C$_{10}$ alkyl, —OC(O)C$_2$–C$_{10}$ alkenyl, —OC(O)C$_2$–C$_{10}$ alkynyl, —N(hydrogen, $C_1$–$C_{10}$ alkyl, $C_2$–$C_{10}$ alkenyl or $C_2$–$C_{10}$ alkynyl)C(O)(C$_1$–C$_{10}$ alkyl, $C_2$–$C_{10}$ alkenyl or $C_2$–$C_{10}$ alkynyl), —C(O)N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), —N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), $C_1$–$C_{10}$ alkoxy, $C_6$–$C_{10}$ aryl and 5–10 membered heterocyclic;

n is an integer from 0 to 5;

$R^6$ is hydrogen or methyl;

each $R^7$ is independently hydrogen, $C_1$–$C_{20}$ alkyl, $C_2$–$C_{20}$ alkenyl, $C_2$–$C_{20}$ alkynyl, —C(O)C$_1$–C$_{20}$ alkyl, —C(O)C$_2$–C$_{20}$ alkenyl, —C(O)C$_2$–C$_{20}$ alkynyl, —C(O)N(H)C$_1$–C$_{10}$ alkyl, —C(O)N(H)C$_2$C$_{20}$ alkenyl, —C(O)N(H)C$_2$–C$_{20}$ alkynyl, —SO$_2$(O)C$_1$–C$_{20}$ alkyl, —SO$_2$(O)C$_1$–C$_{20}$ alkenyl, —SO$_2$(O)C$_2$–C$_{20}$ alkynyl or —PO$_4^{2-}$;

$R^8$ is hydrogen or methyl;

$R^9$ is

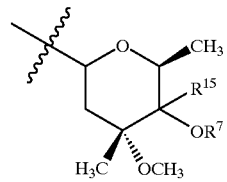

or 4"-oxocladinosyl;

$R^{10}$ is an alpha-branched $C_2$–$C_8$ alkyl, alkenyl, alkynyl, alkoxyalkyl or alkylthioalkyl group, any of which may optionally be substituted by one or more hydroxyl groups; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methyl or one or more hydroxyl, one or more $C_1$–$C_4$ alkyl groups or halo atoms; or a 3 to 6 membered oxygen or sulphur containing heterocyclic ring which may be saturated, or fully or partially unsaturated and which may optionally be substituted by one or more $C_1$–$C_4$ alkyl groups or halo atoms; or $R^{10}$ is phenyl which may be optionally substituted with at least one substituent selected from the group consisting of $C_1$–$C_4$ alkyl, $C_1$–$C_4$ alkylthio groups, halogen atoms, hydroxyl groups, trifluoromethyl, and cyano; or $R^{10}$ may be with a formula (a)j as shown below:

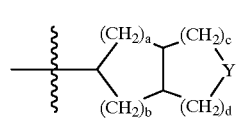

wherein

Y is O, S or —CH$_2$—, a, b, c, and d is each independently an integer ranging from 0 to 2 and a+b+c+d≦5;

$R^{11}$ is hydrogen or —OH; and $R^{15}$ is H, $C_1$–$C_{10}$ alkyl, $C_2$–$C_{10}$ alkenyl, $C_2$–$C_{10}$ alkynyl, cyano, —CH$_2$S(O)$_p$C$_1$–C$_{10}$ alkyl, —CH$_2$S(O)$_p$C$_2$–C$_{10}$ alkenyl, —CH$_2$S(O)$_p$C$_2$–C$_{10}$ alkynyl, wherein p is an integer ranging from 0 to 2, —CH$_2$O(C$_1$–C$_{10}$ alkyl), —CH$_2$O(C$_2$–C$_{10}$ alkenyl), —CH$_2$O(C$_2$–C$_{10}$ alkynyl), —CH$_2$N(hydrogen, $C_1$–$C_{10}$ alkyl, $C_2$–$C_{10}$ alkenyl or $C_2$-alkynyl)(hydrogen, $C_1$–$C_{10}$ alkyl, $C_2$–$C_{10}$ alkenyl or $C_2$–$C_{10}$ alkynyl), —(CH$_2$)$_m$(C$_6$–C$_{10}$ aryl) or —(CH$_2$)$_m$(5–10 membered heteroaryl), wherein m is an integer ranging from 0 to 4, and wherein the alkyl, alkenyl, alkynyl, aryl and heteroaryl moieties of the foregoing are optionally substituted with 1 to 3 substituents independently selected from the group consisting of halo, cyano, nitro, trifluoromethyl, azido, —C(O)C$_1$–C$_{10}$ alkyl, —C(O)C$_2$–C$_{10}$ alkenyl, —C(O)C$_2$–C$_{10}$ alkynyl, —OC(O)C$_2$–C$_{10}$ alkenyl, —OC(O)C$_2$–C$_{10}$ alkynyl, —N(hydrogen, $C_1$–$C_{10}$ alkyl, $C_2$–$C_{10}$ alkenyl or $C_2$–$C_{10}$ alkynyl)C(O)($C_1$–$C_{10}$ alkyl, $C_2$–$C_{10}$ alkenyl or $C_2$–$C_{10}$ alkynyl), —C(O)N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), —N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynl), $C_1$–$C_{10}$ alkoxy, $C_6$–$C_{10}$ aryl or 5–10 membered heterocyclic, hydroxy, $C_1$–$C_6$ alkyl, $C_1$–$C_6$ alkoxy, $C_6$–$C_{10}$ aryl and 5–10 membered heteroaryl, which comprises the step of contacting a compound of the formula 5

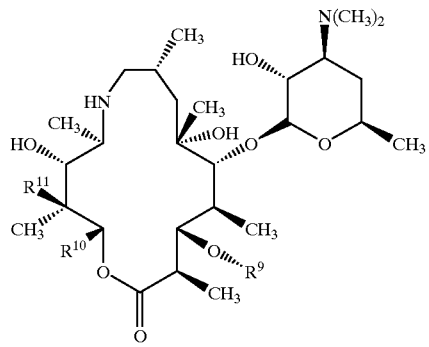

5 wherein $R^9$, $R^{10}$ and $R^{11}$ are defined above, with an acid or a base, to result in the formation of the compound of formula 15.

31. A method of preparing a compound of the formula 15

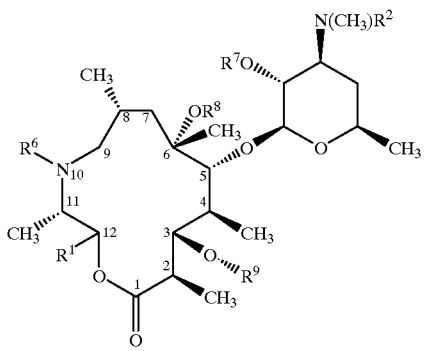

15 or a pharmaceutically acceptable salt thereof, wherein:

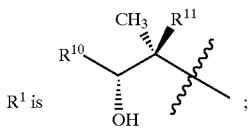

$R^1$ is $R^2$ is hydrogen or $C_1$–$C_4$ alkyl;

$R^3$ is hydrogen, $C_1$–$C_{10}$ alkyl, $C_2$–$C_{10}$ alkenyl, $C_2$–$C_{10}$ alkynyl, —($CH_2$)$_m$($C_6$–$C_{10}$ aryl), or —($CH_2$)$_m$($C_6$–$C_{10}$ heterocyclic), each, other than hydrogen, being optionally substituted with 1 to 3 substituents independently selected from the group consisting of halogen, cyano, nitro, trifluoromethyl, azido, —C(O)$C_1$–$C_{10}$ alkyl, —C(O)$C_2$–$C_{10}$ alkenyl, —C(O)$C_2$–$C_{10}$ alkynyl, —OC(O)$C_1$–$C_{10}$ alkyl, —OC(O)$C_2$–$C_{10}$ alkenyl, —OC(O)$C_2$–$C_{10}$ alkynyl, —N(hydrogen, $C_1$–$C_{10}$ alkyl, $C_2$–$C_{10}$ alkenyl or $C_2$–$C_{10}$ alkynyl)C(O)($C_1$–$C_{10}$ alkyl, $C_2$–$C_{10}$ alkenyl or $C_2$–$C_{10}$ alkyl, —C(O)N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), —N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), $C_1$–$C_{10}$ alkoxy, $C_6$–$C_{10}$ aryl, 5–10 membered heterocyclic, hydroxyl, methoxyl, $C_1$–$C_{10}$ alkyl, $C_2$–$C_{10}$ alkenyl, $C_2$–$C_{10}$ alkynyl, 2-pyridyl, 3-pyridyl, 4-pyridyl, 2-pyrimidyl, 4-pyrimidyl, 2-pyridylmethyl, 3-pyridylmethyl, 4-pyridylmethyl, 2-pyridylethyl, 3-pyridylethyl and 4-pyridylethyl;

m is an integer ranging from 0 to 4;

each $R^4$ is hydrogen, —($CH_2$)$_m$($C_6$–$C_{10}$ aryl) or —($CH_2$)$_m$($C_6$–$C_{10}$ heterocyclic), each, other than hydrogen, being optionally substituted with 1 to 3 substituents independently selected from the group consisting of halo, cyano, nitro, trifluoromethyl, azido, —C(O)$C_1$–$C_{10}$ alkyl, —C(O)$C_2$–$C_{10}$ alkenyl, —C(O)$C_2$–$C_{10}$ alkynyl, —OC(O)$C_1$–$C_{10}$ alkyl, —OC(O)$C_2$–$C_{10}$ alkenyl, —OC(O)$C_2$–$C_{10}$ alkynyl, —N(hydrogen, $C_1$–$C_{10}$ alkyl, $C_2$–$C_{10}$ alkenyl or $C_2$–$C_{10}$ alkynyl)C(O)($C_1$–$C_{10}$ alkyl, $C_2$–$C_{10}$ alkenyl or $C_2$–$C_{10}$ alkynyl), —C(O)N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), —N(hydrogen, $C_1$–$C_{10}$ alkyl, $C_2$–$C_{10}$ alkenyl or $C_2$–$C_{10}$ alkynyl)(hydrogen, $C_1$–$C_{10}$ alkyl, $C_2$–$C_{10}$ alkenyl or $C_2$–$C_{10}$ alkynyl), $C_1$–$C_{10}$ alkoxy, $C_6$–$C_{10}$ aryl and 5–10 membered heterocyclic;

n is an integer from 0 to 5;

$R^6$ is hydrogen or methyl;

each $R^7$ is independently hydrogen, $C_1$–$C_{20}$ alkyl, $C_2$–$C_{20}$ alkenyl, $C_2$–$C_{20}$ alkynyl, —C(O)$C_1$–$C_{20}$ alkyl, —C(O)$C_2$–$C_{20}$ alkenyl, —C(O)$C_2$–$C_{20}$ alkynyl, —C(O)N(H)$C_1$–$C_{10}$ alkyl, —C(O)N(H)$C_2$–$C_{20}$ alkenyl, —C(O)N(H)$C_2$–$C_{20}$ alkynyl, —SO$_2$(O)$C_1$–$C_{20}$ alkyl, —SO$_2$(O)$C_2$–$C_{20}$ alkenyl, —SO$_2$(O)$C_2$–$C_{20}$ alkynyl or —PO$_4^{2-}$;

$R^8$ is hydrogen or methyl;

$R^9$ is

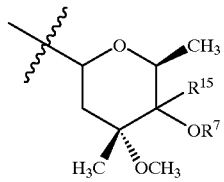

or 4"-oxocladinosyl;

$R^{10}$ is an alpha-branched $C_2$–$C_8$ alkyl, alkenyl, alkynyl, alkoxyalkyl or alkylthioalkyl group, any of which may optionally be substituted by one or more hydroxyl groups; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methyl or one or more hydroxyl, one or more $C_1$–$C_4$ alkyl groups or halo atoms; or a 3 to 6 membered oxygen or sulphur containing heterocyclic ring which may be saturated, or fully or partially unsaturated and which may optionally be substituted by one or more $C_1$–$C_4$ alkyl groups or halo atoms; or $R^{10}$ is phenyl which may be optionally substituted with at least one substituent selected from the group consisting of $C_1$–$C_4$ alkyl, $C_1$–$C_4$ alkylthio groups, halogen atoms, hydroxyl groups, trifluoromethyl, and cyano; or $R^{10}$ may be with a formula (a) as shown below:

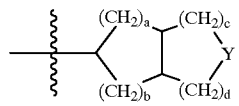

a wherein

Y is O, S or —CH$_2$—, a, b, c, and d is each independently an integer ranging from 0–2 and a+b+c+d≦5;

$R^{11}$ is hydrogen or —OH; and $R^{15}$ is H, $C_1$–$C_{10}$ alkyl, $C_2$–$C_{10}$ alkenyl, $C_2$–$C_{10}$ alkynyl, cyano, —CH$_2$S(O)$_p$C$_1$–C$_{10}$ alkyl, —CH$_2$S(O)$_p$C$_2$–C$_{10}$ alkenyl, —CH$_2$S(O)$_p$C$_2$–C$_{10}$ alkynyl, wherein p is an integer ranging from 0 to 2, —CH$_2$O(C$_1$–C$_{10}$ alkyl), —CH$_2$O(C$_2$–C$_{10}$ alkenyl), —CH$_2$O(C$_2$–C$_{10}$ alkynyl), —CH$_2$N(hydrogen, C$_1$–C$_{10}$ alkyl, C$_2$–C$_{10}$ alkenyl or C$_2$–C$_{10}$ alkynyl)(hydrogen, C$_1$–C$_{10}$ alkyl, C$_2$–C$_{10}$ alkenyl or C$_2$–C$_{10}$ alkynyl), —(CH$_2$)$_m$(C$_6$–C$_{10}$ aryl) or —(CH$_2$)$_m$(5–10 membered heteroaryl), wherein m is an integer ranging from 0 to 4, and wherein the alkyl, alkenyl, alkynyl, aryl and heteroaryl moieties of the foregoing are optionally substituted with 1 to 3 substituents independently selected from the group consisting of halo, cyano, nitro, trifluoromethyl, azido, —C(O)C$_1$–C$_{10}$ alkyl, —C(O)C$_2$–C$_{10}$ alkenyl, —C(O)C$_2$–C$_{10}$ alkynyl, —OC(O)C$_1$–C$_{10}$ alkyl, —OC(O)C$_2$–C$_{10}$ alkenyl, —OC(O)C$_2$–C$_{10}$ alkynyl, —N(hydrogen, C$_1$–C$_{10}$ alkyl, C$_2$–C$_{10}$ alkenyl or C$_2$–C$_{10}$ alkynyl)C(O)(C$_1$–C$_{10}$ alkyl, C$_2$–C$_{10}$ alkenyl or C$_2$–C$_{10}$ alkynyl), —C(O)N(hydrogen, C$_1$–C$_{10}$ alkyl, C$_2$–C$_{10}$ alkenyl or C$_2$–C$_{10}$ alkynyl)(hydrogen, C$_1$–C$_{10}$ alkyl, C$_2$–C$_{10}$ alkenyl or C$_2$–C$_{10}$ alkynyl), —N(hydrogen, C$_1$–C$_{10}$ alkyl, C$_2$–C$_{10}$ alkenyl or C$_2$–C$_{10}$ alkynyl)(hydrogen, C$_1$–C$_{10}$ alkyl, C$_2$–C$_{10}$ alkenyl or C$_2$–C$_{10}$ alkynyl), C$_1$–C$_{10}$ alkoxy, C$_6$–C$_{10}$ aryl or 5–10 membered heterocyclic, hydroxy, C$_1$–C$_6$ alkyl, C$_{11}$–C$_6$ alkoxy, C$_6$–C$_{10}$ aryl and 5–10 membered heteroaryl, which comprises the step of heating a compound of the formula 5

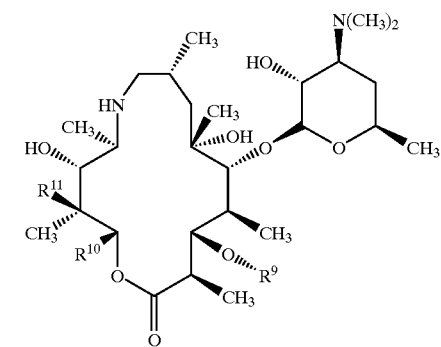

5 wherein $R^9$, $R^{10}$ and $R^{11}$ are as defined above;

in the presence of a solvent system, to result in the formation of the compound of formula 15.

32. The method of any of claims 28, 29, or 31 wherein the solvent system comprises a solvent selected from the group consisting of lower alkanols, diethyl ether, acetone, acetonitrile, tetrahydrofuran, ethyl acetate, benzene, toluene, chloroform, metheylene chloride, dimethylformamide, dimethylsulfoxide, N-methylpyrrolidinone, and mixtures thereof.

33. The method of any of claims 28, 29, or 31 wherein the solvent system further comprises a protic solvent.

34. The method of claim 33 wherein the protic solvent is selected from the group consisting of methanol, ethanol, n-propanol, iso-propanol, n-butanol, iso-butanol, sec-butanol, phenol, halophenols, naphthols, water, and mixtures thereof.

* * * * *